US006630577B2

(12) United States Patent
Stolowitz et al.

(10) Patent No.: US 6,630,577 B2
(45) Date of Patent: Oct. 7, 2003

(54) 1,2-PHENYLENEDIBORONIC ACID REAGENTS AND COMPLEXES

(75) Inventors: Mark L. Stolowitz, Woodinville, WA (US); Guisheng Li, Bothell, WA (US); Jean P. Wiley, Woodinville, WA (US)

(73) Assignee: Prolinx, Inc., Bothell, WA (US)

( * ) Notice: Subject to any disclaimer, the term of this patent is extended or adjusted under 35 U.S.C. 154(b) by 0 days.

(21) Appl. No.: 09/874,633

(22) Filed: Jun. 4, 2001

(65) Prior Publication Data

US 2002/0038004 A1 Mar. 28, 2002

Related U.S. Application Data

(63) Continuation-in-part of application No. 09/625,231, filed on Jul. 25, 2000, now Pat. No. 6,462,179, which is a division of application No. 09/407,673, filed on Sep. 28, 1999, now Pat. No. 6,124,471, which is a division of application No. 09/138,105, filed on Aug. 21, 1998, now Pat. No. 6,075,126, which is a continuation-in-part of application No. 08/689,283, filed on Aug. 5, 1996, now Pat. No. 5,837,878, and a continuation-in-part of application No. 08/689,341, filed on Aug. 5, 1996, now Pat. No. 5,847,192.

(51) Int. Cl.[7] .................................................. C07F 5/02

(52) U.S. Cl. .................... 530/391.1; 435/174; 435/181; 436/532; 530/345; 530/350; 530/391.7; 530/402; 530/810; 530/816; 536/17.1; 536/23.1; 536/24.3; 536/24.5; 558/288; 558/289; 558/290; 562/7

(58) Field of Search .......................... 424/450; 435/174, 435/181; 530/345, 350, 391.1, 391.7, 402, 810, 816; 536/17.1, 23.1, 24.3, 24.5; 548/405; 558/288, 289, 290; 562/7

(56) References Cited

U.S. PATENT DOCUMENTS 5,594,111 A 1/1997 Stolowitz ................. 530/391.1
5,594,151 A 1/1997 Stolowitz ..................... 548/542
5,623,055 A 4/1997 Stolowitz ................. 530/391.1
5,648,470 A 7/1997 Stolowitz ................. 530/391.1
5,668,257 A 9/1997 Stolowitz ................. 530/391.1
5,668,258 A 9/1997 Stolowitz ................. 530/391.1
5,688,928 A 11/1997 Stolowitz ................. 530/391.1
5,744,727 A 4/1998 Hanneborg et al. ........... 73/733
5,777,148 A 7/1998 Stolowitz et al. ........... 558/399
5,831,045 A 11/1998 Stolowitz et al. .......... 536/22.1
5,831,046 A 11/1998 Stolowitz et al. .......... 536/22.1
5,837,878 A 11/1998 Stolowitz et al. ........... 558/315
5,847,192 A 12/1998 Stolowitz et al. ........... 558/399
5,852,178 A 12/1998 Stolowitz ..................... 530/402
5,859,210 A 1/1999 Stolowitz et al. ........ 530/391.1
5,869,623 A 2/1999 Stolowitz et al. ........ 530/391.1
5,872,224 A 2/1999 Stolowitz et al. ........ 530/396.1
5,876,938 A 3/1999 Stolowitz et al. .............. 439/6
5,877,297 A 3/1999 Stolowitz et al. ........ 530/391.1
6,008,406 A 12/1999 Stolowitz ....................... 562/7
6,013,783 A 1/2000 Kaiser et al. .............. 536/23.1
6,031,117 A 2/2000 Kaiser et al. ............... 552/105
6,075,126 A * 6/2000 Stolowitz et al. ........ 530/391.1
6,124,471 A * 9/2000 Stolowitz et al. ........... 548/405
6,462,179 B1 * 10/2002 Stolowitz et al. ........ 530/391.1

OTHER PUBLICATIONS

Nozaki, K., et al., "A Chiral Lewis Acid with Two "Metal" Centers: Cooperative Binding of Two Amine Molecules to a Chiral Diboronic Ester," Angew. Chem. Int. Ed. Engl. 1994, No. 23/24, pp. 2452–2454.

Nozaki, K., et al., "Chiral Bimetallic Boronic Esters: A Donor–Acceptor Coexisting Receptor for Amines," Bull. Chem. Soc. Jpn., 69, (1996), pp. 2043–2052.

* cited by examiner

*Primary Examiner*—Richard L. Raymond
(74) *Attorney, Agent, or Firm*—Blakely Sokoloff Taylor & Zafman LLP

(57) ABSTRACT

A reagent having the general formula of General Formula I:

General Formula I

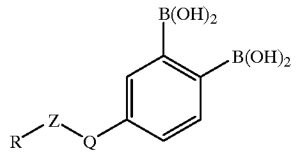

wherein group Z comprises a spacer selected from an aliphatic chain up to about 6 carbon equivalents in length, an unbranched aliphatic chain of from about 6 to 18 carbon equivalents in length with at least one of an intermediate amide and a disulfide moiety, and a polyethylene glycol chain of from about 3 to 12 carbon equivalents in length; wherein group R is an electrophilic or nucleophilic moiety suitable for reaction of the reagent with a biologically active species; and wherein group Q is one of nothing at all, an amide, a methyl amide, a methylene, an ether, a thioether, a methyl ether, and a methyl thioether moiety. Also, a conjugate, a bioconjugate and a method of conjugating.

27 Claims, 9 Drawing Sheets

General Formula I

General Formula II

General Formula III

General Formula IV

General Formula I

General Formula II

General Formula V

General Formula VI

ANALYSIS A

ANALYSIS B

1,2-PHENYLENEDIBORONIC ACID REAGENTS AND COMPLEXES

CROSS-REFERENCE TO RELATED APPLICATION

The present application is a Continuation-In-Part of U.S. patent application Ser. No. 09/625,231 (now U.S. Pat. No. 6,462,179), filed Jul. 25, 2000 by applicants, Mark L. Stolowitz, Edward A. Kesicki, Kevin P. Lund, and Karin A. Hughes, titled "Phenyldiboronic Acid Reagents and Complexes", which is a divisional application of U.S. patent application Ser. No. 09/407,673. filed on Sep. 28, 1999 (now U.S. Pat. No. 6,124,471), which is a divisional of U.S. patent application Ser. No. 09/138,105, filed on Aug. 21, 1998 (now U.S. Pat. No. 6.075,126) which is a continuation in part of U.S. patent application Ser. No. 08/689,283, filed on Aug. 5, 1996 (now U.S. Pat. No. 5,837,878), and continuation in part of U.S. patent application Ser. No. 08/689,341, filed on Aug. 5, 1996 (now U.S. Pat. No. 5,847,192).

FIELD OF THE INVENTION

The present invention relates to the field of bioconjugate preparation, and more particularly, to a novel class of 1,2-phenylenediboronic acid (1,2-PDBA) reagents useful for the conjugation of biological macromolecules, and the method of making and using such reagents.

BACKGROUND OF THE INVENTION

Bioconjugation is a descriptive term for the joining of two or more different molecular species by chemical or biological means, in which at least one of the molecular species is a biological macromolecule. This includes, but is not limited to, conjugation of proteins, peptides, polysaccharides, hormones, nucleic acids, liposomes and cells, with each other or with any other molecular species that add useful properties, including, but not limited to, drugs, radionuclides, toxins, haptens, inhibitors, chromophores, fluorophores, ligands, etc. Immobilization of biological macromolecules is also considered a special case of bioconjugation in which the macromolecule is conjugated, either reversibly or irreversibly, to an insoluble support including a chromatographic support. Bioconjugation is utilized extensively in biochemical, immuno-chemical and molecular biological research. Major applications of bioconjugation include, but are not limited to, detection of gene probes, enzyme-linked immunological solid-phase assay, monoclonal antibody drug targeting and medical imaging.

Bioconjugates are generally classified as either direct or indirect conjugates. Direct conjugates encompass those in which two or more components are joined by direct covalent chemical linkages. Alternatively, indirect conjugates encompass those in which two or more components are joined via an intermediary complex involving a biological macromolecule.

Avidin-biotin System

Although numerous methods of indirect bioconjugate preparation have been described, a significant number of those reported in the literature have been prepared by exploiting the Avidin-Biotin system. In the Avidin-Biotin system, the binding specificity of the protein Avidin (purified from egg white), or Streptavidin (purified from the bacterium *Streptomyces avidinii*), toward the cofactor Biotin (vitamin H) is utilized to bridge an Avidin conjugated macromolecule with a biotinylated macromolecule. Both Avidin and Streptavidin possess four Biotin binding sites of very high affinity ($K_d$=$10^{-15}$ $mol^{-1}$).

The Avidin-Biotin system has been utilized extensively for enzyme-linked immuno-logical solid-phase assay (ELISA), in which an enzyme-Avidin conjugate (useful for detection by reaction with the enzyme's substrate to afford a colored or chemiluminescent product) is employed to detect the presence of a biotinylated antibody, after first binding the antibody to an immobilized antigen or hapten. Applications of the Avidin-Biotin system number in the hundreds, and have recently been reviewed (Wilchek, M. and Bayer, E. A., (1990) *Methods in Enzymology,* 184).

Although utilized extensively, several limitations are known to be associated with the Avidin-Biotin system, which include nonspecific binding generally attributed to the basicity of the Avidin molecule, nonspecific binding attributed to the presence of carbohydrate residues on the Avidin molecule, and background interference associated with the presence of endogenous Biotin, which is ubiquitous in both eukaryotic and prokaryotic cells.

Digoxigenin Anti-digoxigenin System

An alternative indirect bioconjugation system designed to overcome some of the limitations associated with the Avidin-Biotin system has recently been developed for the detection of gene probes by ELISA. See Kessler, C., Hôltke, H.-J., Seibl, R., Burg, J. and Mühlegger, K., *Biol. Chem. Hoppe-Seyler* (1990), 371, 917–965. This system involves the use of the steroid hapten Digoxigenin, an alkaloid occurring exclusively in Digitalis plants, and Fab fragments derived from polyclonal sheep antibodies against Digoxigenin (anti-Digoxigenin). The high specificity of the various anti-Digoxigenin antibodies affords low backgrounds and eliminates the non-specific binding observed in Avidin-Biotin systems. Digoxigenin-labeled DNA and RNA probes can detect single-copy sequences in human genomic Southern blots. The development of the Digoxigenin anti-Digoxigenin system has recently been reviewed. See Kessler, C. (1990) in Advances in Mutagenesis Research (Obe, G. ed.) pp. 105–152, Springer-Verlag, Berlin and Heidelberg. The Digoxigenin anti-Digoxigenin system is the most recent representative of several hapten-antibody systems now routinely utilized for bioconjugation.

Immobilized Phenylboronates

Phenylboronic acids are known to interact with a wide range of polar molecules having certain requisite functionalities. Complexes of varying stability, involving 1,2-diols, 1,3-diols, 1,2-hydroxy acids, 1,3-hydroxy acids, 1,2-hydroxylamines, 1,3-hydroxylamines, 1,2-diketones and 1,3-diketones, are known to form with either neutral phenylboronic acid or the phenylboronate anion. Consequently, immobilized phenylboronic acids have been exploited as chromatographic supports to selectively retain, from diverse biological samples, those molecular species having the requisite functionalities. Many important biological molecules including carbohydrates, catecholamines, prostaglandins, ribonucleosides, and steroids contain the requisite functionalities, and have been either analyzed or purified in this manner. The use of phenylboronic acid chromatographic media for the isolation and separation of biological molecules has been discussed in several reviews. See Singhal, R. P. and DeSilva, S. S. M., *Adv. Chromatog.* (1989), 31, 293–335; Mazzeo, J. R. and Krull, I. S., *BioChromatog.* (1989), 4, 124–130; and Bergold, A. and Scouten, W. H. (1983) in Solid Phase Biochemistry (Scouten, W. H. ed.) pp. 149–187, John Wiley & Sons, New York.

Phenylboronic acid, like boric acid, is a Lewis acid, and ionizes not by direct deprotonation, but by hydration to give the tetrahedral phenylboronate anion ($pK_a$=8.86). Phenylboronic acid is three times as strong an acid as boric acid. Ionization of phenylboronic acid is an important factor in complex formation, in that, upon ionization, boron changes from trigonal coordination (having average bond angles of 120° and average bond lengths of 1.37 angstroms) to the tetrahedral coordination (having average bond angles of 109° and average bond lengths of 1.48 angstroms).

Molecular species having cis or coaxial 1,2-diol and 1,3-diol functionalities, and particularly carbohydrates, are known to complex with immobilized phenylboronate anion, to form cyclic esters under alkaline aqueous conditions. See Lorand, J. P. and Edwards, J. O., *J. Org. Chem.* (1959), 24, 769.

Acidification of 1,2-diol and 1,3-diol complexes to neutral pH is know to release the diol containing species, presumably due to hydrolysis of the cyclic ester. Coplanar aromatic 1,3-diols, like 1,8-dihydroxynaphthalene, are known to complex even under acidic conditions due to the hydrolytic stability of six-membered cyclic boronic acid esters. See Sienkiewicz, P. A. and Roberts, D. C., *J. Inorg. Nucl. Chem.* (1980), 42, 1559–1571.

Molecular species having pendant 1,2-hydroxylamine, 1,3-hydroxylamine, 1,2-hydroxy-amide, 1,3-hydroxyamide, 1,2-hydroxyoxime and 1,3-hydroxyoxime functionalities are also known to reversibly complex with phenylboronic acid under alkaline aqueous conditions similar to those associated with the retention of diol containing species. See Tanner, D. W. and Bruice, T. C., *J. Amer. Chem. Soc.* (1967), 89, 6954.

General Methods for the Preparation of Phenylboronic Acids and Phenylenediboronic Acids The most popular methods of synthesizing phenylboronic acids involve in situ generation of arylmagnesium or aryllithium species from aryl halides followed by transmetalation with a trialkoxyborate. See Todd, M. H., Balasubramanian, S. and Abell, C., *Tetrahedron Lett.* (1997), 38, 6781–6784; Thompson, W. and Gaudino, J., *J. Org. Chem.* (1984), 49, 5237–5243; Crisofoli, W. A. and Keay, B. A., *Tetrahedron Lett.* (1991), 32, 5881–5884; Sharp, M. J., Cheng, W. and Sniekus, V., *Tetrahedron Lett.* (1987), 28, 5093–5096; and Larson, R. D., King, A. O., Cheng, C. Y., Corley, E. G., Foster, B. S., Roberts, F. E., Yang, C., Lieberman, D. R., Reamer, R. A., Tschaen, D. M., Verhoeven, T. R. and Reider, P. J., *J. Org. Chem.* (1994), 59, 6391–6394.

Recently, transition-metal catalyzed cross coupling reactions have been developed to produce phenylboronic acids from aryl halides and alkoxydiboron, see Ishiyama, T., Murata, M. and Miyaura, N., *J. Org. Chem.* (1995), 60, 7508–7510; Giroux, A., Han, Y. and Prasit, P., *Tetrahedran Lett.* (1997), 38, 3841–3844, or dialkoxyhydroborane, see Murata, M.; Watanabe, S.; Masuda, Y., *J. Org. Chem.* (1997), 62, 6458–6459 using $PdCl_2$ (dppf) as the catalyst. Additionally, a palladium-catalyzed solid-phase boronation, using alkoxydiboron, has also been reported using a polymer-bound aryl halide. See Piettre, S. R. and Baltzer, S., *Tetrahedron Lett.* (1997), 38, 1197–1200.

The preparation of 1,2-phenylenediboronic acid has been previously described on only one occasion (Clement, R., Thiais, F., *Hebd. Seances Acad. Sci., Ser. C* (1966), 263, 1398–400. The preparation of 1,2-phenylenediboronate complexes prepared from 2,2'-(1,2-phenylene)bis-[(4R,5R)-4,5-diphenyl-1,3,2-dioxaborolane], involving addition of either one or two equivalents of benzylamine, has been recently described. See Nozaki, K., Yoshida, M. and Takaya, H., *Angew. Chem. Int. Ed. Engl.* (1994), 33, 2452–2454 and Nozaki, K., Yoshida, M. and Takaya, H., *Bull. Chem. Soc. Jpn.* (1996), 69, 2043–2052.

Phenylboronate Bioconjugates

2-Acetamidophenylboronic acids have been proposed as potential linkers for selective bioconjugation via the vicinal diol moieties of the carbohydrate residues associated with glycoproteins. See Cai, S. X. and Keana, J. F. W., *Bioconjugate Chem.* (1991), 2, 317–322. Phenylboronic acid bioconjugates derived from 3-isothiocyanatophenylboronic acid have been successfully utilized for appending radioactive technetium dioxime complexes to monoclonal antibodies for use in medical imaging. See Linder, K. E., Wen, M. D., Nowotnik, D. P., Malley, M. F., Gougoutas, J. Z., Nunn, A. D. and Eckelman, W. C., *Bioconjugate Chem.* (1991), 2, 160–170; Linder, K. E., Wen, M. D., Nowotnik, D. P., Ramalingam, K., Sharkey, R. M., Yost, F., Narra, R. K. and Eckelman, W. C., *Bioconjugate Chem.* (1991), 2, 407–414.

3-Aminophenylboronic acid has been covalently appended to proteins by a variety of chemical methods and the resulting phenylboronic acid bioconjugates tested for their binding of D-sorbitol, D-mannose and glycated hemoglobin (GHb). The interactions proved to be reversible and of very low affinity rendering the bioconjugates of very limited practical use. Similarly, an Alkaline Phosphatase-phenylboronate bioconjugate used in an attempted enzyme-linked assay for the detection of GHb failed to detect the presence of glycated protein. See Frantzen, F., Grimsrud, K., Heggli, D. and Sundrehagen, E., *Journal of Chromatography B* (1995), 670, 37–45.

In addition to attempts to utilize immobilized phenylboronates for chromatographic separation of biological molecules having the requisite functionalities, a novel class of phenylboronic acid reagents, phenyldiboronic acid reagents, and boronic and diboronic compound complexing reagents have been developed for conjugating biologically active species (or bioactive species) and exploiting indirect bioconjugation through reversible formation of a boronic acid complex. These reagents and associated conjugates may be used in a manner analogous to Avidin-Biotin and Digoxigenin-anti-Digoxigenin systems. However, unlike the Avidin-Biotin and Digoxigenin-anti-Digoxigenin systems where the viability of the biological macromolecule must be maintained to preserve requisite binding properties, the bioconjugate formed through the boron complex is generally insensitive to significant variations in ionic strength, temperature, the presence of organic solvents, and the presence of chaotropic agents (protein and nucleic acid denaturants). Phenylboronic acid reagents and boronic compound complexing reagents, their conjugates and bioconjugates as well as methods for their preparation and use are the subject of U.S. Pat. Nos. 5,594,111, 5,623,055, 5,668,258, 5,648,470, 5,594,151, 5,668,257, 5,688,928, 5,744,727, 5,777,148, 5,831,045, 5,831,046, 5,837,878, 5,847,192, 5,852,178, 5,859,210, 5,869,623, 5,872,224, 5,876,938, 5,877,297, and 6,008,406. 1,3- and 1,4-phenylene diboronic acid reagents and 1,3- and 1,4-diboronic compound complexing reagents, their conjugates and bioconjugates as well as methods for their preparation and use are the subject of U.S. Pat. Nos. 6,075,126, 6,124,471, and 6,156,884.

Phosphoramidite reagents containing protected 1,2-phenylenediboronic acid moieties for the preparation of modified synthetic oligonucleotides are the subject of U.S. Pat. No. 6,031,117. Oligonucleotides and polynucleotides containing 1,2-phenylenediboronic acid moieties, prepared from the aforementioned phosphoramidite reagents, are the subject of U.S. Pat. No. 6,013,783.

Notwithstanding the substantial amount of research into bioconjugation, and the substantial amount of investment in this field, the selectivity of 1,2-phenylenediboronic acid has not heretofore been successfully exploited to enable the conjugation of biological macromolecules (other than synthetic oligonucleotides and polynucleotides) with one another or with other molecular species that add useful properties.

SUMMARY OF THE INVENTION

The present invention relates to a novel class of 1,2-phenylenediboronic acid (1,2-PDBA) reagents useful for the preparation of bioconjugates, and the method of making and using such reagents. In one embodiment, the 1,2-PDBA reagents of the present invention are preferably complexed with boronic compound complexing reagents derived from salicylhydroxamic acid (SHA), or derivatives thereof. In a second embodiment, the 1,2-PDBA reagents of the present invention are preferably complexed with boronic compound complexing reagents derived from 2,6-dihydroxybenzohydroxamic acid (DHBHA), or derivatives thereof.

In the present invention, in the place of prior art Avidin-Biotin and Digoxigenin anti-Digoxigenin systems, 1,2-PDBA reagents are utilized in conjunction with boronic compound complexing reagents to facilitate chemical conjugation without the use of intermediary biological macromolecules. Bioconjugate preparation often involves the conjugation of several components including, but not limited to, proteins, peptides, polysaccharides, hormones, nucleic acids, liposomes and cells, with each other or with any other molecular species that add useful properties, including, but not limited to, drugs, radionuclides, toxins, haptens, inhibitors, fluorophores, ligands, and solid-phase supports including chromatographic supports. These various components utilized in bioconjugate preparation will collectively and individually be termed biologically active species or bioactive species.

Reagents suitable for the modification of a bioactive species for the purpose of incorporating one or more 1,2-phenylenediboronic acid moieties for subsequent conjugation to a different (or the same) bioactive species having one or more pendant boronic compound complexing moieties are of General Formula I, General Formula I

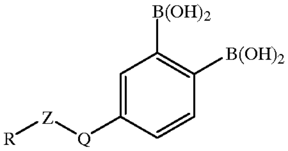

wherein group R is a reactive electrophilic or nucleophilic moiety suitable for reaction of the 1,2-phenylenediboronic acid reagent with a bioactive species. Group Z is a spacer and group Q is an optional linkage that includes one of amide, ether and thioether moieties.

Reagents of General Formula I exhibit superior properties when compared to prior art phenylboronic acid reagents, in that, they incorporate two equivalents of boronic acid per reactive group R, and afford complexes in conjunction with boronic compound complexing reagents that exhibit superior stability in aqueous systems.

Reaction of a reagent of General Formula I with a bioactive species affords a conjugate having pendant 1,2-phenylenediboronic acid moieties (one or more) of General Formula II, General Formula II

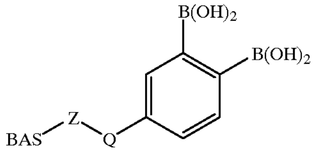

wherein the symbol labeled BAS represents a biologically active species (or bioactive species) that may or may not contain a portion of a reactive moiety (which may itself have a spacer) used to attach the bioactive species to the reagent. Group Z in General Formula II is a spacer and group Q is an optional linkage that includes one of amide, ether and thioether moieties. It will be appreciated that, in many embodiments, several identical reagents of the general formula of General Formula I will react with a single BAS molecule. For example, if the BAS is a protein, many 1,2-PDBA reagents will react with the protein, each reacting at one of the several sites on the protein which are reactive with the R group of the 1,2-PDBA reagent. A representative illustration of multiple 1,2-PDBA reagents reacted with a biologically active species (or bioactive species) includes the following:

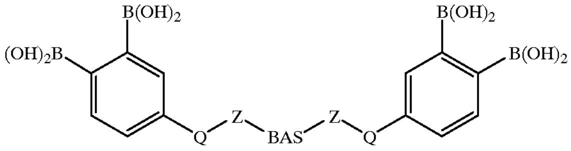

Conjugates of General Formula II exhibit reduced hydrophobic secondary properties as compared to phenylboronic acid conjugates known in the prior art. This reduction in hydrophobic secondary properties lowers the extent of non-specific binding, which is known to be a problem associated with bioactive species that have been conjugated with several hydrophobic moieties.

To form an indirect bioconjugate without the use of an intermediary macromolecule the conjugate of General Formula II may be complexed with a boronic compound complexing conjugate. For example, boronic compound complexing reagents may be appended to a biologically active species to afford a conjugate having pendant boronic compound complexing moieties (one or more) of the general formula of General Formula III, General Formula III

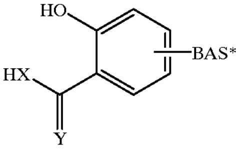

wherein the symbol labeled BAS* represents a second bioactive species, that may include a linker portion and that may differ from the bioactive species labeled BAS. The BAS* may also include a portion of a reactive moiety used to attach the bioactive species to the boronic compound complexing reagent. Group X is an acidic electron pair donating species, and group Y is selected from one of O, S and NH.

A conjugate of General Formula II, with at least one biologically active species and having pendent 1,2-phenylenediboronic acid moieties (one or more), may be complexed with one or more conjugates of General Formula III, prepared from a second bioactive species BAS*, and having pendant boronic compound complexing moieties (one or more), to afford, for example, a bioconjugate of General Formula IV, General Formula IV

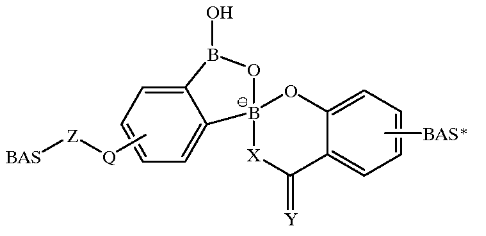

wherein the symbols labeled BAS and BAS*, and groups Z and Q are as were previously defined. Group X is an acidic electron pair donating species, and group Y is selected from one of O, S and NH. In this manner, biological macromolecules may be conjugated to one another or with other functionalities that impart useful properties.

Alternatively, boronic compound complexing reagents may be appended to a biologically active species to afford a conjugate having pendant boronic compound complexing moieties (one or more) of General Formula V, General Formula V

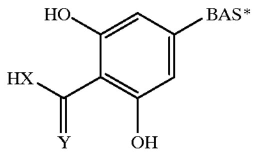

wherein the symbol labeled BAS* represents a second bioactive species, that may include a linker portion and that may differ from the bioactive species labeled BAS. The BAS* may also include a portion of a reactive moiety used to attach the bioactive species to the boronic compound complexing reagent. Group X is an acidic electron pair donating species, and group Y is selected from one of O, S and NH.

A conjugate of General Formula II, with at least one biologically active species and having pendent 1,2-phenylenediboronic acid moieties (one or more), may be complexed with one or more conjugates of General Formula V, prepared from a second bioactive species BAS*, and having pendant boronic compound complexing moieties (one or more), to afford, for example, a bioconjugate of General Formula VI, General Formula VI

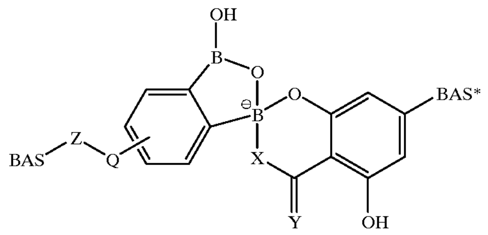

wherein the symbols labeled BAS and BAS*, and groups Z and Q are as were previously defined. Group X is an acidic electron pair donating species, and group Y is selected from one of O, S and NH. In this manner, biological macromolecules may be conjugated to one another or with other functionalities that impart useful properties.

Bioconjugates of General Formulas IV and VI may be prepared in buffered aqueous solution or organic solvents. The bioconjugate is formed within a few minutes over a range of temperatures of from about 4° C. to 70° C. The stability of the bioconjugate in aqueous solution at a given pH and temperature is significantly influenced by groups X and Y.

The bioconjugation reaction (boronic acid complexation) is generally insensitive to significant variations in ionic strength, the presence of organic solvents, the presence of detergents, and the presence of chaotropic agents (protein denaturants), which are incompatible with prior art indirect labeling systems wherein the structure of a biological macromolecule must be maintained to preserve requisite binding properties. In most instances, the constraints governing the formation of bioconjugates, by the system herein described, are limited to those imposed by the conditions required to maintain viability (native conformation) of the bioactive species.

DETAILED DESCRIPTION

Figure 1:
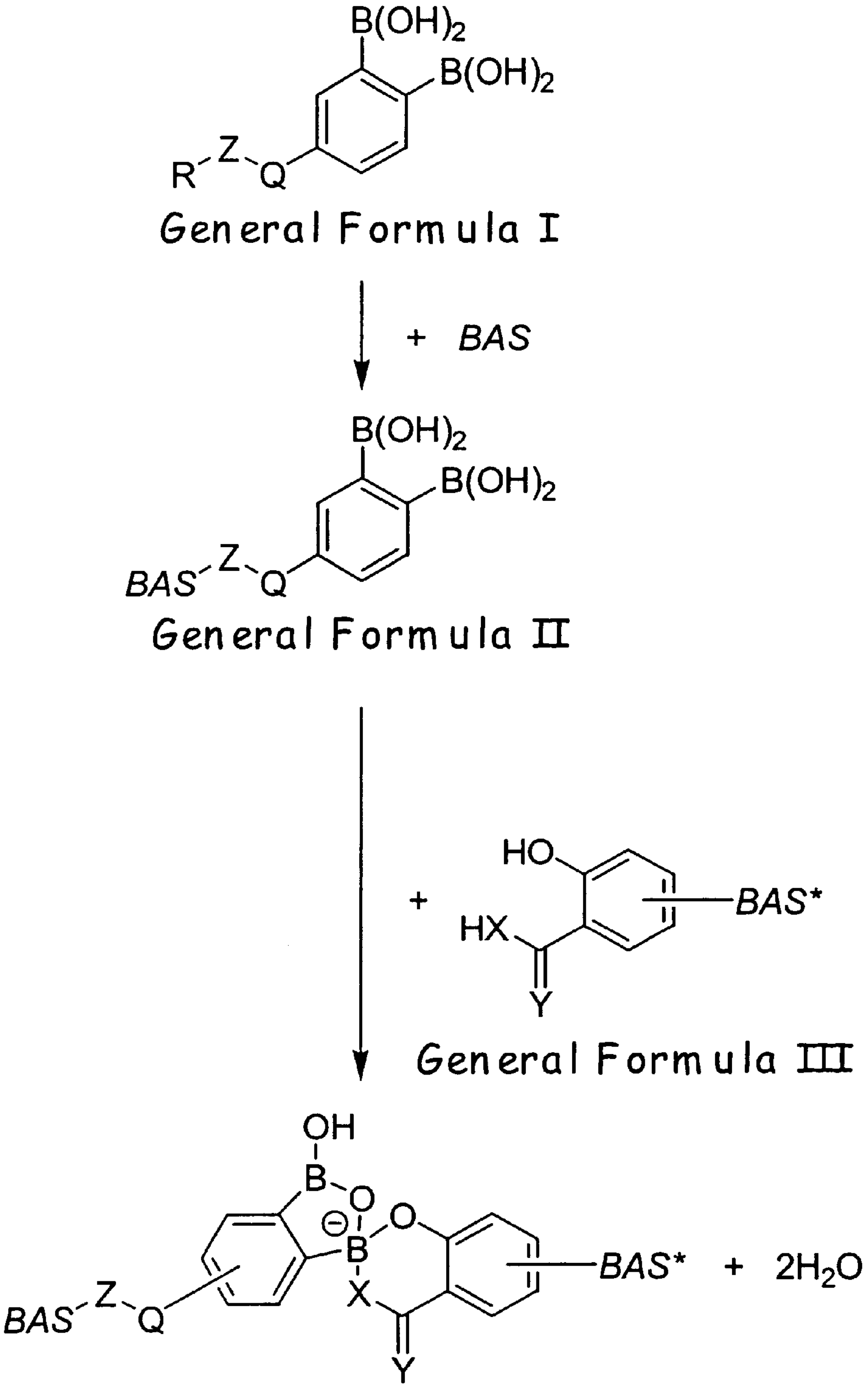
FIG. 1 illustrates the utilization of 1,2-PDBA reagents of General Formula I to prepare conjugates of General Formula II. Conjugates of General Formula II may be utilized, in turn, in conjunction with boronic compound complexing conjugates of General Formula III, to prepare bioconjugates of General Formula IV.

Reagents suitable for the modification of a bioactive species for the purpose of incorporating one or more 1,2-phenylenediboronic acid moieties for subsequent conjugation to a different (or the same) bioactive species having one or more pendant boronic compound complexing moieties are of General Formula I, General Formula I

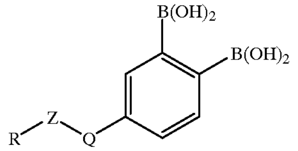

wherein group R is a reactive electrophilic or nucleophilic moiety suitable for reaction of the 1,2-phenylenediboronic acid reagent with a bioactive species. Group Z is a spacer selected from a saturated or unsaturated aliphatic chain up to about 0 to 6 carbon equivalents in length, an unbranched saturated or unsaturated aliphatic chain of from about 6 to 18 carbon equivalents in length with at least one intermediate amide or disulfide moiety, and a polyethylene glycol chain of from about 3 to 12 carbon equivalents in length. Group Q is an optional linkage that includes one of amide, methyl amide, methylene, ether, thioether, methyl ether and methyl thioether moieties.

Group R is preferably selected from, but not limited to, one of amino, acrylamido, bromo, bromoacetamido, chloro, chloroacetamido, dithiopyridyl, hydrazido, N-hydroxysuccinimido ester, N-hydroxysulfosuccinimido ester, imido ester, imidazolo, iodo, iodoacetamido, maleimido and thiol moieties. Group Z is preferably an unbranched alkyl chain of the general formula $(CH_2)_n$, wherein n=1 to 6. Group Q is preferably selected from, with reference to the aromatic ring (Ar) to which the linkage is appended, one of ArCONH, ArNHCO, $ArCH_2$, $ArCH_2CONH$, $ArCH_2NHCO$, $ArNHCOCH_2$, $CONHCH_2$, ArO, $ArCH_2O$, $ArOCH_2$, ArS, $ArCH_2S$ moieties.

Reagents of General Formula I exhibit superior properties when compared to prior art phenylboronic acid reagents, in that, they incorporate two equivalents of boronic acid per reactive group R, and afford complexes in conjunction with boronic compound complexing reagents that exhibit superior stability in aqueous systems.

Reaction of a reagent of General Formula I with a bioactive species affords a conjugate having pendant 1,2-phenylenediboronic acid moieties (one or more) of General Formula II, General Formula II

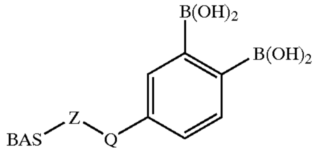

wherein the symbol labeled BAS represents a biologically active species (or bioactive species) that may or may not contain a portion of a reactive moiety (which may itself have a spacer) used to attach the bioactive species to the reagent. It will be appreciated that, in many embodiments, several identical reagents of the general formula of General Formula I will react with a single BAS molecule. For example, if the BAS is a protein, many 1,2-PDBA reagents will react with the protein, each reacting at one of the several sites on the protein which are reactive with the R group of the 1,2-PDBA reagent. Group Z in General Formula II is a spacer selected from an aliphatic chain, such as a saturated or unsaturated chain up to about 0 to 6 carbon equivalents in length, an unbranched saturated or unsaturated aliphatic chain of from about 6 to 18 carbon equivalents in length with at least one intermediate amide and disulfide moieties, and a polyethylene glycol chain of from about 3 to 12 carbon equivalents in length. Group Q is an optional linkage that includes one of amide, methyl amide, methylene, ether, thioether, methyl ether and methyl thioether moieties.

Conjugates of General Formula II exhibit reduced hydrophobic secondary properties as compared to phenylboronic acid conjugates known in the prior art. This reduction in hydrophobic secondary properties lowers the extent of non-specific binding, which is known to be a problem associated with bioactive species that have been conjugated with several hydrophobic moieties.

To form an indirect bioconjugate without the use of an intermediary macromolecule the conjugate of General Formula II may be complexed with a boronic compound complexing conjugate. For example, boronic compound complexing reagents may be appended to a biologically active species to afford a conjugate having pendant boronic compound complexing moieties (one or more) of the general formula of General Formula III, General Formula III

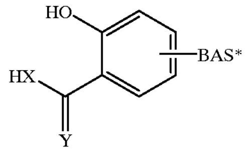

wherein the symbol labeled BAS* represents a second bioactive species, that may include a linker portion and that may differ from the bioactive species labeled BAS (for example, in General Formula II). The BAS* may also include a portion of a reactive moiety used to attach the bioactive species to the boronic compound complexing reagent. Group X is selected from one of O, NH, NR', NOH, and NOR", in which R' is selected from either an alkyl (e.g., methyl, ethyl, etc.), aryl (e.g., phenyl), alkylaryl (e.g., $CH_2C_6H_5$) and a lower alkylene (e.g., methylene, ethylene) bearing an electronegative substituent (e.g., $CH_2CN$, $CH_2COOH$, etc.). Group R" is selected from one of $CH_3$, $CH_2CH_3$, $CH_2CN$, $CH_2CH_2OH$, $CH_2COOH$, $CH_2CONH_2$ and $CH_2OCH_3$Group Y is selected from one of O, S, and NH, and is preferably O.

Conjugates of the general formula of General Formula III, and methods for their preparation are the subject of U.S. Pat. Nos. 5,594,111, 5,623,055, 5,668,258, 5,648,470, 5,594,151, 5,668,257, 5,688,928, 5,744,727, 5,847,192, 5,852,178, 5,859,210, 5,869,623, 5,872,224, 5,877,297 and 6,008,406.

A conjugate of General Formula II, with at least one biologically active species and having pendent 1,2-phenylenediboronic acid moieties (one or more), may be complexed with one or more conjugates of General Formula III, prepared from a second bioactive species BAS*, and having pendant boronic compound complexing moieties (one or more), to afford, for example, a bioconjugate of General Formula IV, General Formula IV

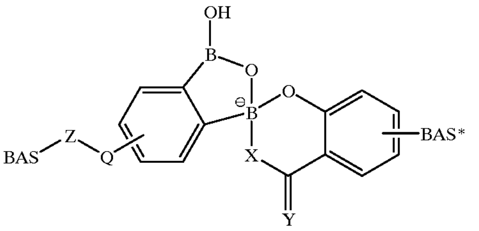

wherein the symbols labeled BAS and BAS*, and groups Z and Q are as were previously defined. Group X is selected from one of O, NH, NR', NOH, and NOR", in which R' is selected from either an alkyl (e.g., methyl, ethyl, etc.), aryl (e.g., phenyl), alkylaryl (e.g., $CH_2C_6H_5$) and a methylene or ethylene bearing an electronegative substituent (e.g., $CH_2CN$, $CH_2COOH$, etc.). Group R" is preferably selected from one of $CH_3$, $CH_2CH_3$, $CH_2CN$, $CH_2CH_2OH$, $CH_2COOH$, $CH_2CONH_2$ and $CH_2OCH_3$. Group Y is selected from one of O, S, and NH, and is preferably O. In this manner, biological macromolecules may be conjugated to one another or with other functionalities that impart useful properties.

Alternatively, boronic compound complexing reagents may be appended to a biologically active species to afford a conjugate having pendant boronic compound complexing moieties (one or more) of General Formula V, General Formula V

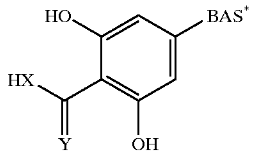

wherein the symbol labeled BAS* represents a second bioactive species, that may include a linker portion and that may differ from the bioactive species labeled BAS (for example, in General Formula II). The BAS* may also include a portion of a reactive moiety used to attach the bioactive species to the boronic compound complexing reagent. Group X is selected from one of O, NH, NR', NOH, and NOR", in which R' is selected from either an alkyl (e.g., methyl, ethyl, etc.), aryl (e.g., phenyl), alkylaryl (e.g., $CH_2C_6H_5$) and a methylene or ethylene bearing an electronegative substituent (e.g., $CH_2CN$, $CH_2COOH$, etc.). Group R" is selected from one of $CH_3$, $CH_2CH_3$, $CH_2CN$, $CH_2CH_2OH$, $CH_2COOH$, $CH_2CONH_2$ and $CH_2OCH_3$. Group Y is selected from one of O, S, and NH, and is preferably O.

Conjugates of the general formula of General Formula V, and methods for their preparation are the subject of U.S. Pat. Nos. 5,777,148, 5,877,297, 5,837,878, and 5,872,224.

A conjugate of General Formula II, with at least one biologically active species and having pendent 1,2-phenylenediboronic acid moieties (one or more), may be complexed with one or more conjugates of General Formula V, prepared from a second bioactive species BAS*, and having pendant boronic compound complexing moieties (one or more), to afford, for example, a bioconjugate of General Formula VI, General Formula VI

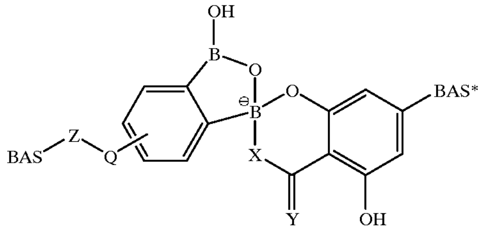

wherein the symbols labeled BAS and BAS*, and groups Z and Q are as were previously defined. Group X is selected from one of O, NH, NR', NOH, and NOR", in which R' is selected from either an alkyl (e.g., methyl, ethyl, etc.), aryl (e.g., phenyl), alkylaryl (e.g., $CH_2C_6H_5$) and a methylene or ethylene bearing an electronegative substituent (e.g., $CH_2CN$, $CH_2COOH$, etc.). Group R" is preferably selected from one of $CH_3$, $CH_2CH_3$, $CH_2CN$, $CH_2CH_2OH$, $CH_2COOH$, $CH_2CONH_2$ and $CH_2OCH_3$. Group Y is selected from one of O, S, and NH, and is preferably O. In this manner, biological macromolecules may be conjugated to one another or with other functionalities that impart useful properties.

Bioconjugates of General Formulas IV and VI, derived form 1,2-phenylenediboronic acids, differ structurally from those obtained by reaction of boronic compound complexing reagents with either phenylboronic acids, 1,3-phenylenediboronic acids or 1,4-phenylene-diboronic acids, in that the boronic acid complex is significantly stabilized, with respect to both alkaline- and acid-catalyzed hydrolysis, by an elimination reaction whereby the free hydroxyl group appended to boron that is normally associated with the boronic acid complex is esterified to the adjacent 1,2-boronic acid group resulting in formation of a five-member ring fused to the aryl ring and containing the fragment B—O—B, wherein the complexed boronic acid is in the tetrahedral anionic form and the adjacent boronic acid is in the trigonal neutral form. Phosphoramidite reagents containing protected 1,2- and 1,3-phenylenediboronic acid moieties for the preparation of modified synthetic oligonucleotides, and oligonucleotides and polynucleotides containing 1,2- and 1,3-phenylenediboronic acid moieties prepared from the aforementioned phosphoramidite reagents, are the subject of U.S. Pat. Nos. 6,031,117 and 6,013,783, respectively. Reagents prepared from 1,3- and 1,4-phenylenediboronic acids are described in U.S. Pat. Nos. 6,075,126 and 6,124,471, titled "Phenyldiboronic Acid Reagents and Complexes," filed Aug. 21, 1998, and Sep. 28, 1999, respectively, which are incorporated herein by reference.

Preparation of Bioconjugates of General Formulas IV and VI

Bioconjugates of General Formulas IV and VI may be prepared in buffered aqueous solution or organic solvents. Preferred buffers include acetate, citrate, phosphate, carbonate and diglycine. Borate buffers should be avoided due to their ability to complex with the boronic compound complexing moiety. Tris(hydroxymethyl)aminomethane, β-hydroxyamine and β-hydroxyacid buffers should be avoided due to their ability to competitively complex with the 1,2-phenylenediboronic acid. The bioconjugate is formed within a few minutes over a range of temperatures of from about 4° C. to 70° C. The stability of the bioconjugate in aqueous solution at a given pH and temperature is significantly influenced by groups X and Y. For example, bioconjugates of General Formula IV, wherein X is NOH and Y is O (derived from salicylhydroxamic acid), are stable in aqueous solutions of approximate pH greater than 4.5 and less than 12.5. Bioconjugates of General Formula VI, wherein X is NOH and Y is O (derived from 2,6-dihydroxybenzohydroxamic acid), are stable in aqueous solutions of approximate pH greater than 2.5 and less than 12.5. Consequently, bioconjugates of General Formula VI are preferred when working in buffered aqueous solutions at low pH.

The bioconjugation reaction (boronic acid complexation) is insensitive to significant variations in ionic strength, the presence of organic solvents, the presence of detergents, and the presence of chaotropic agents (protein denaturants), which are incompatible with prior art indirect labeling systems wherein the structure of a biological macromolecule must be maintained to preserve requisite binding properties. In most instances, the constraints governing the formation of bioconjugates, by the system herein described, are limited to those imposed by the conditions required to maintain viability (native conformation) of the bioactive species.

The process which utilizes 1,2-phenylenediboronic acid reagents of General Formula I for the preparation of bioconjugates is summarized in FIG. 1. Initially, a 1,2-phenylenediboronic acid reagent of General Formula I is selected that is comprised of an appropriate reactive electrophilic or nucleophilic group R, suitable for reaction with a desired biologically active species (or bioactive species).

General Formula I

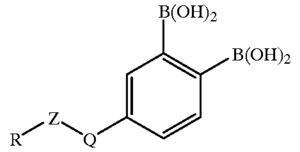

Group R is a reactive electrophilic or nucleophilic moiety suitable for reaction of the 1,2-phenylenediboronic acid reagent with a bioactive species, and is preferably selected from, but not limited to, one of amino, acrylamido, bromo, bromoacetamido, chloro, chloroacetamido, dithiopyridyl, hydrazido, N-hydroxysuccinimido ester, N-hydroxysulfosuccinimido ester, imido ester, imidazolo, iodo, iodoacetamid, maleimid and thiol moieties. Group Z is a spacer, and group Q is an optional linkage that, when present, includes one of amide, methyl amide, methylene, ether, thioether, methyl ether and methyl thioether moieties.

The 1,2-phenylenediboronic acid reagent of General Formula I is condensed with the bioactive species to yield an 1,2-phenylenediboronic acid conjugate of General Formula II, General Formula II

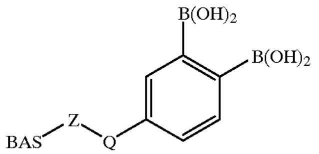

wherein the symbol labeled BAS represents a biologically active species (or bioactive species) that may or may not contain a portion of a reactive moiety (which may itself have a spacer) used to attach the bioactive species to the reagent. It will be appreciated that, in many embodiments, several identical reagents of the general formula of General Formula I will react with a single BAS molecule. For example, if the BAS is a protein, many 1,2-PDBA reagents will react with the protein, each reacting at one of the several sites on the protein which are reactive with the R group. Group Z is a spacer, and group Q is an optional linkage that, when present, includes one of amide, methyl amide, methylene, ether, thioether, methyl ether and methyl thioether moieties.

The 1,2-phenylenediboronic acid conjugate of General Formula II is complexed with a boronic compound complexing conjugate. An example of a suitable boronic compound complexing conjugate is derived from salicylhydroxamic acid (SHA) and is of the general formula of General Formula III, General Formula III

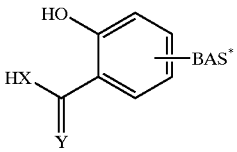

wherein the symbol labeled BAS* represents a second biologically active species, that may include a linker portion and differ from the biologically active species labeled BAS of the complexing reagent. The BAS* may also include a portion of a reactive moiety used to attach the bioactive species to the boronic compound complexing reagent. The reaction yields a complex of General Formula IV, General Formula IV

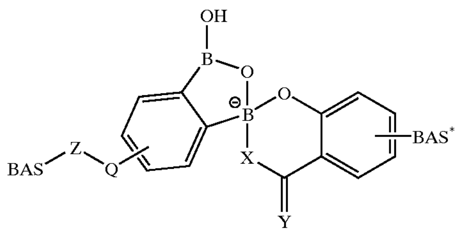

wherein the symbols labeled BAS and BAS*, and groups Z and Q are as were previously defined. Group X is selected from one of O, NH, NR', NOH, and NOR", in which R' is selected from either an alkyl (e.g., methyl, ethyl, etc.), aryl (e.g., phenyl), alkylaryl (e.g., $CH_2C_6H_5$) and a methylene or ethylene bearing an electronegative substituent (e.g., $CH_2CN$, $CH_2COOH$, etc.). Group R" is selected from one of $CH_3$, $CH_2CH_3$, $CH_2CN$, $CH_2CH_2OH$, $CH_2COOH$, $CH_2CONH_2$ and $CH_2OCH_3$. Group Y is selected from one of O, S, and NH, and is preferably O.

Figure 2:
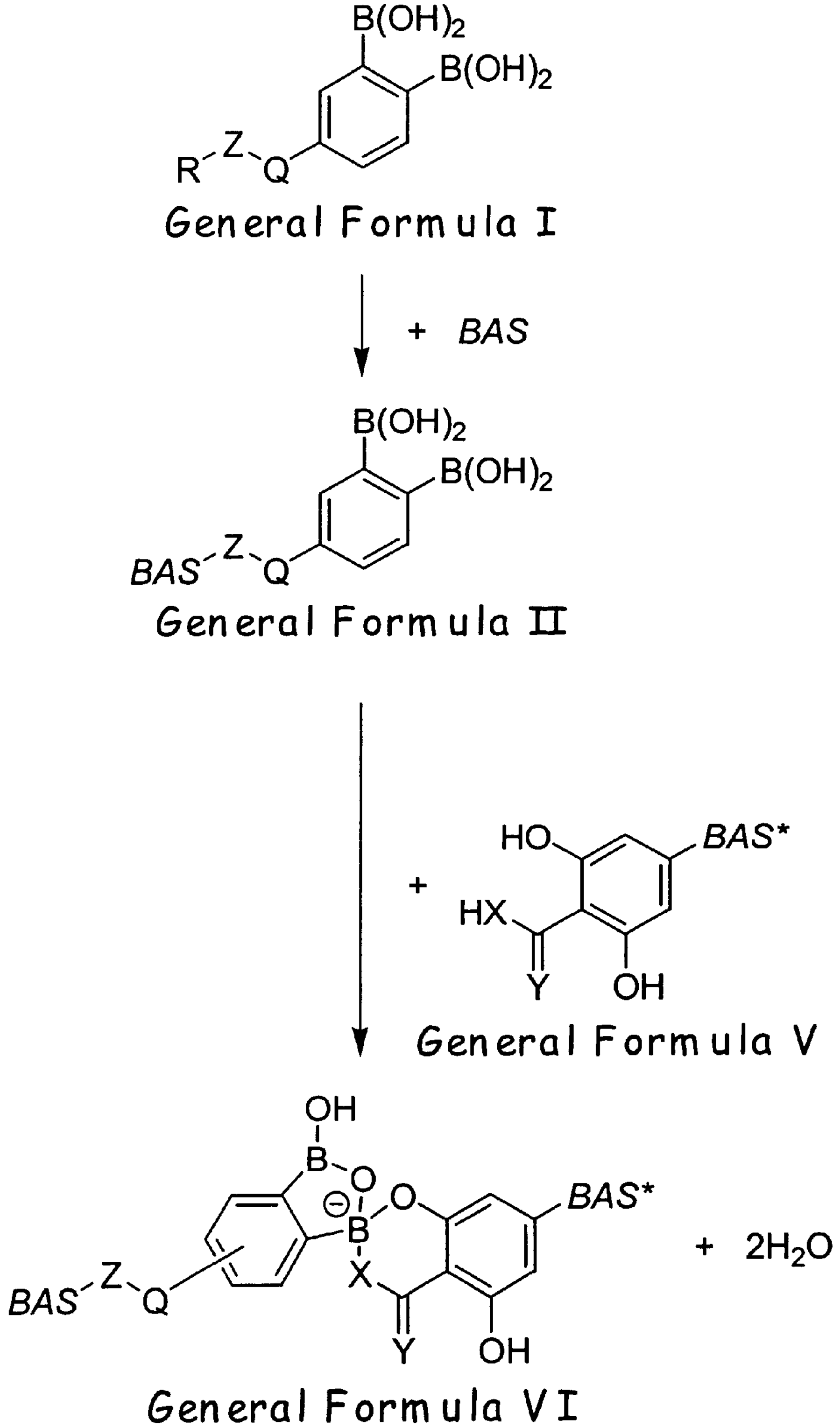
FIG. 2 illustrates the utilization of 1,2-PDBA reagents of General Formula I to prepare conjugates of General Formula II. Conjugates of General Formula II may be utilized, in turn, in conjunction with boronic compound complexing conjugates of General Formula V, to prepare bioconjugates of General Formula VI.

An alternative process which utilizes 1,2-phenylenediboronic acid reagents of General Formula I for the preparation of bioconjugates is summarized in FIG. 2. In this instance, the boronic compound complexing conjugates are derived from 2,6-dihydroxybenzohydroxamic acid (DHBHA). Thus, 1,2-phenylenediboronic acid conjugates of General Formula II may be complexed with boronic compound complexing conjugates of General Formula V to afford bioconjugates of General Formula VI, General Formula VI

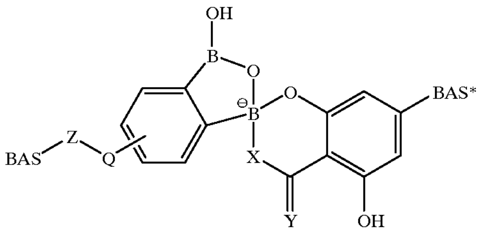

wherein the symbols labeled BAS and BAS*, and groups Z and Q are as were previously defined. Group X is selected from one of O, NH, NR', NOH, and NOR", in which R' is selected from either an alkyl (e.g., methyl, ethyl, etc.), aryl (e.g., phenyl), alkylaryl (e.g., $CH_2C_6H_5$) and a methylene or ethylene bearing an electronegative substituent (e.g., $CH_2CN$, $CH_2COOH$, etc.). Group R" is selected from one of $CH_3$, $CH_2CH_3$, $CH_2CN$, $CH_2CH_2OH$, $CH_2COOH$, $CH_2CONH_2$ and $CH_2OCH_3$. Group Y is selected from one of O, S, and NH, and is preferably O.

Preparation of Reagents of General Formula I

The synthetic routes affording 1,2-phenylenediboronic acid reagents of General Formula I are summarized in FIGS. 3–7. The preferred starting materials for the representative syntheses are either 1,2-dibromo-4-methylbenzene or 1,2-dibromo-4-nitrobenzene.

Figure 3:
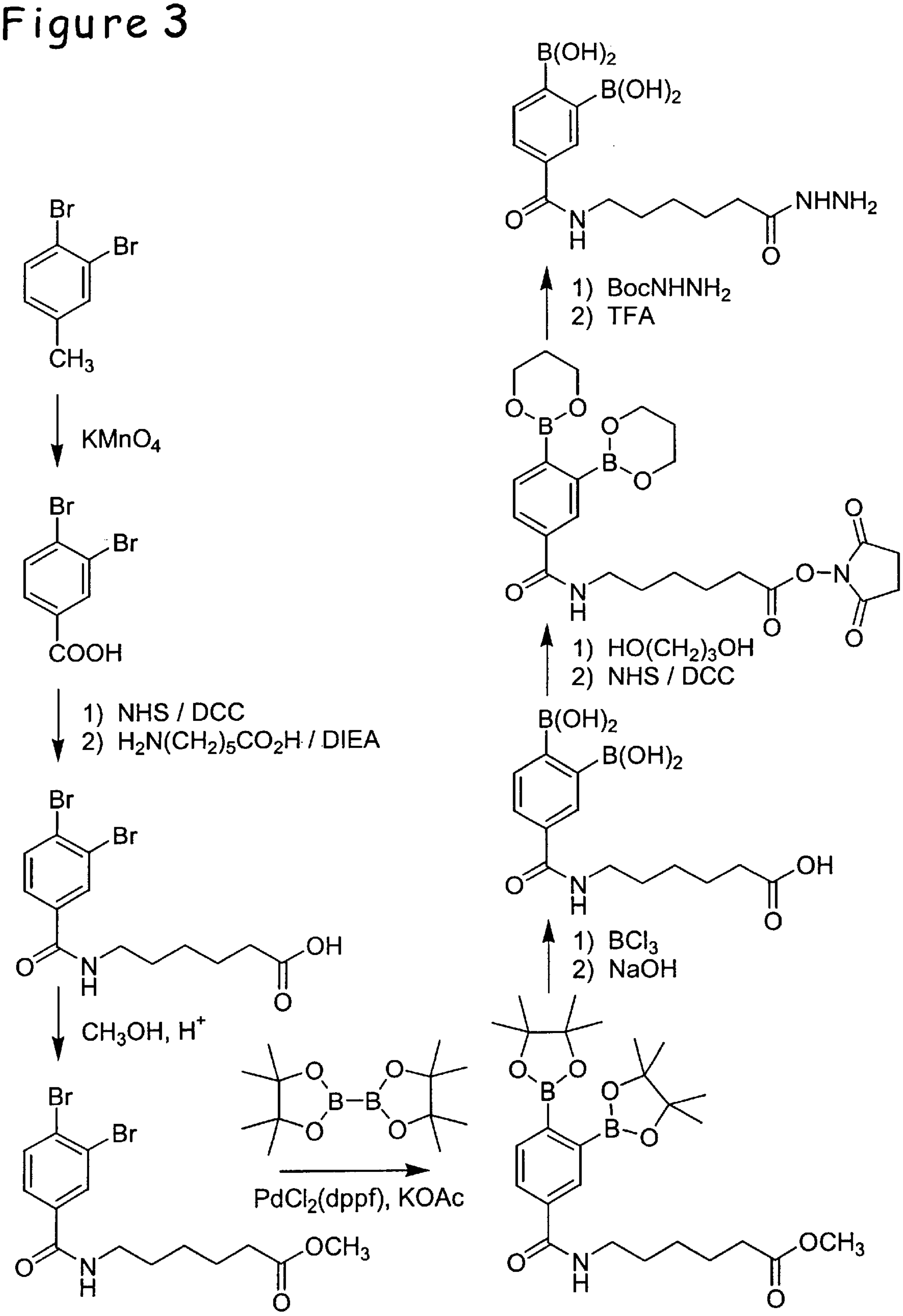
FIG. 3 summarizes the synthetic preparation of 2,5-dioxopyrrolidinyl 6-[(3,4-di(1,3,2-dioxaboran-2-yl)phenyl) carbonylamino]hexanoate and N-amino-6-{[3,4-di (dihydroxyboryl)-phenyl]carbonylamino}hexanamide, reagents of General Formula I wherein Q is an amide derived from an aromatic carboxylic acid, wherein Z is $(CH_2)_5$, and wherein R is either N-hydroxysuccinimido or hydrazido, respectively.

FIG. 3 summarizes the synthetic preparation of 2,5-dioxopyrrolidinyl 6-[(3,4-di(1,3,2-dioxaboran-2-yl)phenyl) carbonylamino]hexanoate and N-amino-6-{[3,4-di (dihydroxyboryl)-phenyl]carbonylamino}hexanamide, preferred reagents of General Formula I. 2,5-dioxo-pyrrolidinyl 6-[(3,4-di(1,3,2-dioxaboran-2-yl)phenyl) carbonylamino]hexanoate represents a reagent of General Formula I wherein the linker Q is an amide moiety, wherein the spacer Z is $(CH_2)_5$, and wherein the reactive group R is an N-hydroxysuccinimidyl ester moiety. Dissolving the reagent in, for example, water yields the unprotected diboronic acid. Alternatively, N-Amino-6-{[3,4-di (dihydroxyboryl)phenyl]carbonylamino}hexanamide represents a reagent of General Formula I wherein the linker Q is an amide moiety, wherein the spacer Z is $(CH_2)_5$, and wherein the reactive group R is a hydrazide moiety. A detailed description of the preparation of 2,5-dioxopyrrolidinyl 6-[(3,4-di(1,3,2-dioxaboran-2-yl)phenyl) carbonylamino]hexanoate is presented in Example I herein. A detailed description of the preparation of N-amino-6-{[3,4-di(dihydroxyboryl)-phenyl]carbonylamino}hexanamide is presented in Example II herein.

Figure 4:
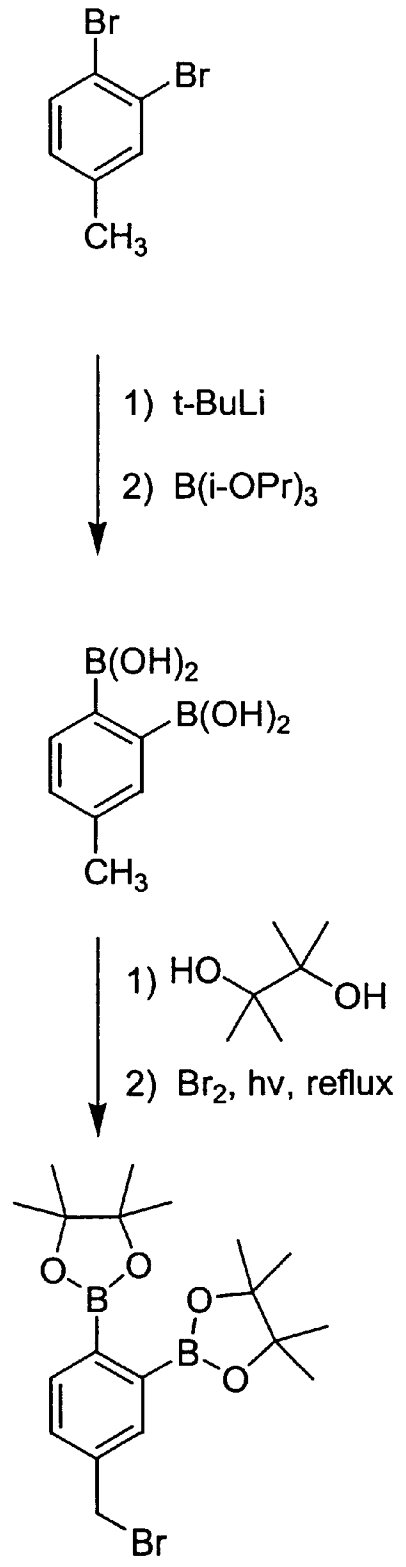
FIG. 4 summarizes the preparation of the synthetic intermediate 2-[5-(bromomethyl)-2-(4,4,5,5-tetramethyl(1,3,2-dioxaborolan-2-yl))phenyl]-4,4,5,5-tetramethyl-1,3,2-dioxaborolane, wherein, relative to the reagent of General Formula I, Q is a methylene, wherein Z is absent, and wherein R is bromo. The reagent depicted in FIG. 4 is also useful as a synthetic intermediate for the preparation of reagents of General Formula I wherein Q is either methyl ether or methyl thioether, as illustrated in FIG. 5.

FIG. 4 summarizes the preparation of the synthetic intermediate 2-[5-(bromomethyl)-2-(4,4,5,5-tetramethyl(1,3,2-dioxaborolan-2-yl))phenyl]-4,4,5,5-tetramethyl-1,3,2-dioxaborolane, which is prepared by boronation of 1,2-dibromo-4-methylbenzene with diboron pinacol diester and [1,1'-bis-(diphenylphosphino)ferrocene]dichloropalladium (II). The intermediate is next protected as the pinacol diester and reacted with bromine in refluxing carbon tetrachloride under an ultraviolet light source to afford the synthetic intermediate.

Figure 5:
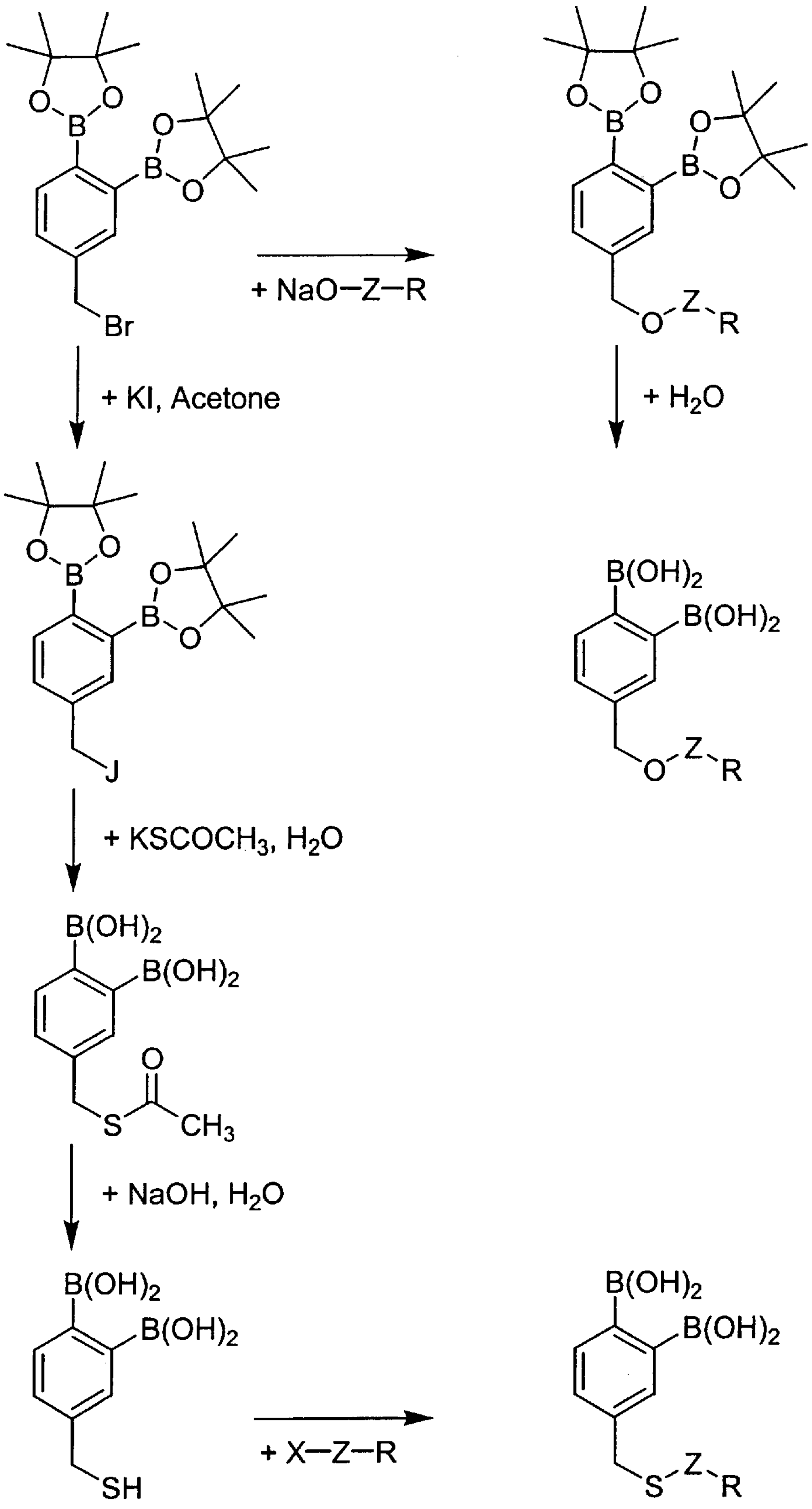
FIG. 5 summarizes the preparation of reagents of General Formula I, derived from 2-[5-(bromomethyl)-2-(4,4,5,5-tetramethyl(1,3,2-dioxaborolan-2-yl))phenyl]-4,4,5,5-tetrameth-1,3,2-dioxaborolane, wherein the linkage Q is either an methyl ether or methyl thioether moiety.

FIG. 5 summarizes the preparation of reagents of General Formula I, wherein the linkage Q is comprised of either an ether or thioether moiety. 2-[5-(Bromomethyl)-2-(4,4,5,5-tetramethyl(1,3,2-dioxaborolan-2-yl))phenyl]-4,4,5,5-tetramethyl-1,3,2-dioxaborolane is treated with excess potassium iodide in acetone to afford 2-[5-(Iodomethyl)-2-(4,4,5,5-tetramethyl(1,3,2-dioxaborolan-2-yl))phenyl]-4,4,5,5-tetramethyl-1,3,2-dioxaborolane which is subsequently alkylated with excess potassium thioacetate to afford 1-{[3,4-di(dihydroxyboryl)phenyl]-methylthio}-ethan-1-one. Treatment of the thioester moiety with aqueous alkaline hydroxyamine liberates the free thiol-containing compound, which may be alkylated with an alkyl halide of the general formula X—Z—R to afford reagents of General Formula I, wherein Q is a thioether moiety. Alternatively, reagents of General Formula I, wherein Q is an ether moiety, may be prepared by classic Williamson ether synthesis, in which, 2-[5-(bromomethyl)-2-(4,4,5,5-tetramethyl(1,3,2-dioxaborolan-2-yl))phenyl]-4,4,5,5-tetramethyl-1,3,2-dioxaborolane, is alkylated with sodium salt of an aliphatic alcohol of the general formula NaO—Z—R as depicted, such as, but not limited to, sodium salts of methy-4-hydroxybutanoate and methyl-6-hydroxyhexanoate.

Figure 6:
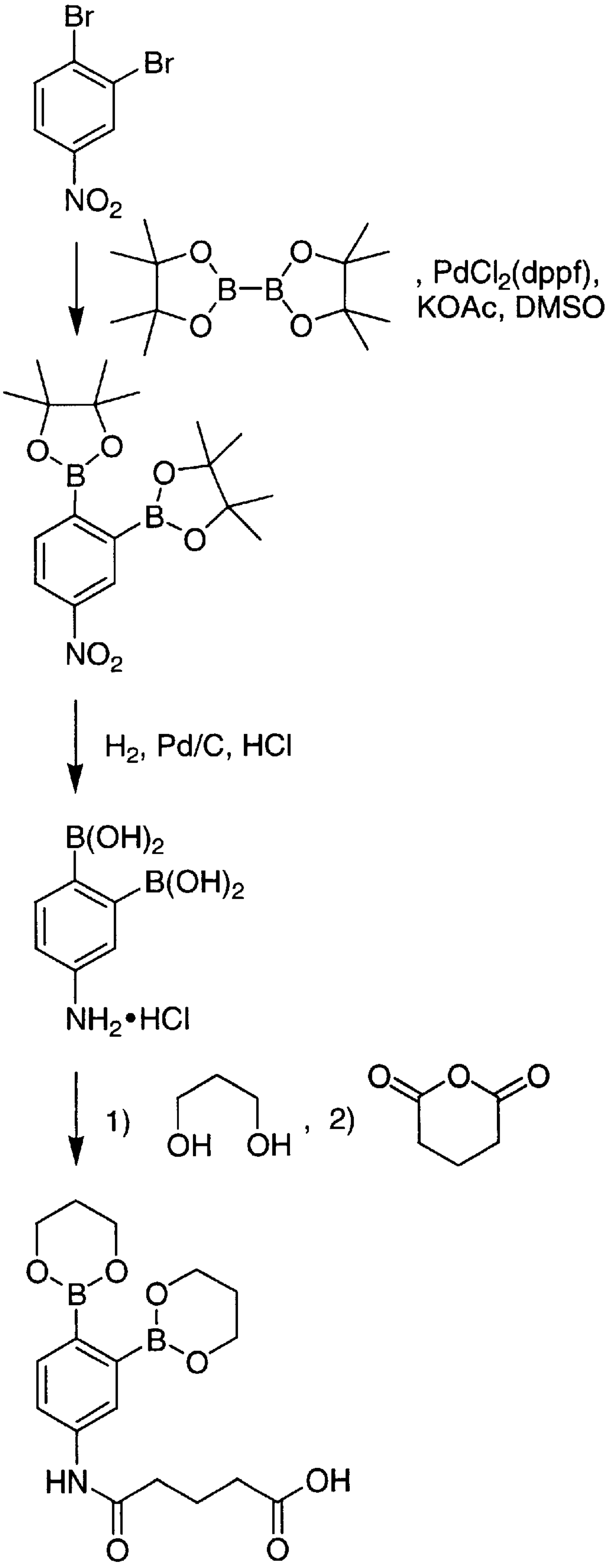
FIG. 6 summarizes the preparation of the synthetic intermediates 1-amino-3,4-di(dihydroxyboryl)benzene hydrochloride and 4-[N-(3,4-di(1,3,2-dioxaboran-2-yl)phenyl)-carbamoyl]butanoic acid, useful for the preparation of reagents of General Formula I wherein Q is an amide derived from an aromatic amine.

FIG. 6 summarizes the preparation of protected reagents of General Formula I, wherein the linkage Q is comprised of an amide moiety derived from an aromatic amine. Initially 1,2-di(dihydroxyboryl)-4-nitrobenzene is reacted with diboron pinacol diester, anhydrous potassium acetate and [1,1'-bis-(diphenylphosphino)-ferrocene]dichloropalladium (II) in anhydrous dimethyl sulfoxide to afford 4,4,5,5-tetramethyl-2-[5-nitro-2-(4,4,5,5-tetramethyl(1,3,2-dioxaborolan-2-yl))phenyl]-1,3,2-dioxaborolane. The intermediary is next reduced by hydrogenation over palladium on carbon in the presence of hydrochloric acid to afford 1-amino-3,4-di(dihydroxyboryl)-benzene hydrochloride. Finally, the 1,2-phenylenediboronic acid is neutralized, protected by dehydration in the presence of excess 1,3- propanediol, and reacted with glutaric anhydride in pyridine to afford 4-[N-(3,4-di(1,3,2-dioxaboran-2-yl)-phenyl) carbamoyl]butanoic acid.

Figure 7:
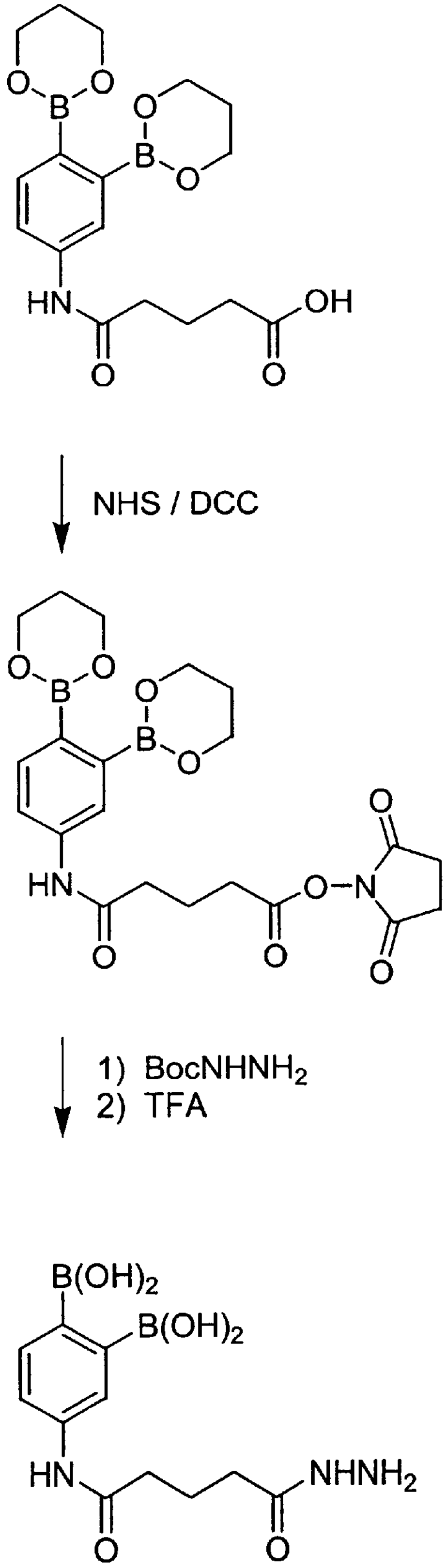
FIG. 7 summarizes the preparation of 2,5-dioxopyrrolidinyl 4-[N-(3,4-di(1,3,2-dioxa-boran-2 -yl) phenyl)carbamoyl]butanoate and N-amino-6-{[3,4-di (dihydroxyboryl)phenylpentane-1,5-diamide, reagents of General Formula I.

FIG. 7 summarizes the preparation of 2,5-dioxopyrrolidinyl 4-[N-(3,4-di(1,3,2-dioxa-boran-2-yl) phenyl)carbamoyl]butanoate and N'-amino-N-[3,4-di (dihydroxyboryl)phenyl]-pentane-1,5-diamide, preferred reagents of General Formula I, prepared from 4-[N-(3,4-di (1,3,2-dioxa-boran-2-yl)phenyl)carbamoyl]butanoic acid. With regard to the 2,5-dioxopyrrolidinyl 4-[N-(3,4-di(1,3,2-dioxaboran-2-yl)-phenyl)carbamoyl]butanoic acid reagent, dissolving the reagent in, for example, water yields the unprotected diboronic acid.

The following examples present a detailed description of the syntheses of reagents of General Formula I, the preparation of conjugates of General Formulas II and V, and the preparation of bioconjugates of General Formulas IV and VI.

EXAMPLE I

Preparation of 2,5-Dioxopyrrolidinyl 6-[(3,4-di(1,3,2-dioxaboran-2-yl)phenyl)-carbonylamino] hexanoate (1,2-PDBA-X-NHS)

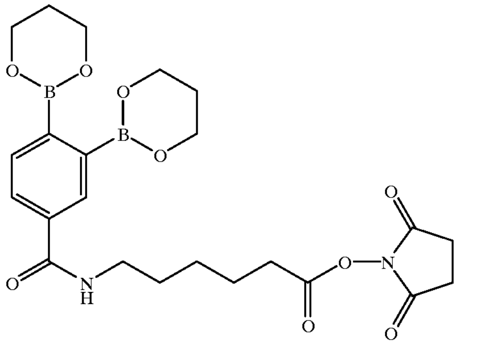

3,4-Dibromobenzoic Acid. A saturated aqueous solution of potassium permanganate (61.3 g, 388 mmol) was added in portions to a well stirred solution of 3,4-dibromotoluene (40.4 g, 162 mmol) in acetic acid (700 mL) while maintaining the temperature between 70 and 80° C. After addition, the suspension was stirred for an additional 4 hours at 80° C. The solution was concentrated on a rotary evaporator, the residue treated with 5 N NaOH (700 mL) and heated under reflux for 2 hours. The $MnO_2$ cake was filtered from solution and washed thoroughly with hot water. The filtrate was extracted with hexane (2×100 mL) and acidified with concentrated HCl pH 2. Collected white precipitate by filtration. Washed precipitate with water and dried under high vacuum. Obtained 16.59 gram (37% yield) of 3,4-dibromobenzoic acid. $^1$H NMR (300 MHz, DMSO-$d_6$): δ13.47 (singlet, 1H), 8.14 (singlet, 1H), 7.88 (doublet, J=8.1 Hz, 1H), 7.99 (doublet, J=8.1 Hz, 1H). $^{13}$C NMR (300 MHz, DMSO-$d_6$): δ165.72, 134.42, 134.18, 132.07, 129.96, 129.32, 124.40.

N-(3,4-Dibromobenzoyl)-6-aminohexanoic Acid. Added N-hydroxysuccinimide (0.69 g, 6 mmol) followed by 1,3-dicyclohexylcarbodiimide (1.24 g, 6 mmol) to a stirred solution of 3,4-dibromobenzoic acid (1.4 g, 5 mmol) in anhydrous dioxane (40 mL). Stirred suspension for 6 hours at room temperature. Filtered precipitate from solution and washed with dioxane (3×5 mL). Combined filtrate and washes and concentrated in vacuo to afford a white solid. Dissolved solid in methanol (50 mL) and added 6-aminohexanoic acid (1.31 g, 10 mmol) and N,N-diisopropylethylamine (1.74 mL, 10 mmol). Stirred for 24 hours at room temperature. Concentrated solution on a rotary evaporator and dissolved residue in 0.1 N NaOH (150 mL). Filtered precipitate from solution and washed with water (2×10 mL). Combined filtrate and washes and acidified with conc. HCl (1.5 mL). Extracted filtrate with ether (2×50 mL), washed extract with brine (2×30 mL) and dried over anhydrous $MgSO_4$. Removed solvent in vacuo to afford a white solid. Obtained 1.78 g (91% yield) of N-(3,4-dibromobenzoyl)-6-aminohexanoic acid. $^1$H NMR (300 MHz, DMSO-$d_6$): δ11.99 (s, 1H), 8.61 (triplet, J=6 Hz, 1H), 8.16 (doublet, J=1.8 Hz, 1H), 7.84(doublet, J=8.1 Hz, 1H), 7.73 (doublet of doublets, J=1.8, 8.1 Hz, 1H), 3.2 (doublet of triplets, J=6,6, 6.0 Hz, 2H), 2.18 (triplet, J=7.3 Hz, 2H), 1.49 (multiplet, 4H), 1.28 (multiplet, 2H). $^{13}$C NMR (300 MHz, DMSO-$d_6$): δ174.71, 164.03, 135.64, 133.98, 132.31, 128.22, 127.20, 124.14, 33.60, 28.65, 26.00, 24.22.

Methyl N-(3,4-Dibromobenzoyl)-6-aminohexanoate. Added conc. $H_2SO_4$ (0.2 mL) to a solution of N-(3,4-dibromobenzoyl)-6-aminohexanoic acid (1.73 g, 4.4 mmol) in methanol (50 mL). Heated under reflux for 2 hours until reaction complete (as determined by TLC). Allowed solution to cool to room temperature and neutralized by adding $NaHCO_3$ solution. Removed solvent in vacuo and extracted residue with ether (2×50 mL). Washed extract with brine (2×30 mL) and dried over anhydrous $MgSO_4$. Filtered extract and dried filtrate under high vacuum to afford a white solid. Obtained 1.72 g (96% yield) of methyl N-(3,4-dibromobenzoyl)-6-aminohexanoate. $^1$H NMR (300 MHz, DMSO-$d_6$): δ8.59 (triplet, J=5.7 Hz, 1H), 8.16 (doublet, J=1.8 Hz, 1H), 7.84 (doublet, J=8.1 Hz, 1H), 7.73 (doublet of doublets, J=8.1, 1.8 Hz, 1H), 3.55 (singlet, 3H), 3.21 (doublet of triplets, J=6.0, 6.6 Hz, 2H), 2.28 (triplet J=7.3 Hz, 2H), 1.51 (multiplet, 4H), 1.28 (multiplet, 2H). $^{13}$C NMR (300 MHz, DMSO-$d_6$): δ173.55, 164.05, 135.67, 133.96, 132.31, 128.20, 127.09, 124.13, 51.19, 39.20, 33.21, 28.56, 25.89, 24.15.

N-[3,4-Bis(dihydroxyboryl)]benzoyl-6-aminohexanoic Acid. Heated a mixture of methyl N-(3,4-dibromobenzoyl)-6-aminohexanoate (1.66 g, 4.08 mmol), diboron pinacol diester (2.49 g, 9.79 mmol), anhydrous potassium acetate (2.40 g, 24.48 mmol), [1,1'-bis(diphenylphosphino)-ferrocen]dichloropalladium (II) (0.60 g, 0.73 mmol) and anhydrous dimethyl sulfoxide (25 mL) under nitrogen for 24 hours at 90° C. Cooled to room temperature and added ethyl acetate (200 mL). Washed successively with water (60 mL), 1 N HCl (2×50 mL) and brine (50 mL). Dried over anhydrous magnesium sulfate. Concentrated in vacuo to afford a black oil (3.22 g). Dissolved oil in dichloromethane (30 mL), cooled to −78° C. and added liquid boron trichloride at −78° C. through a stainless steel cannula. Stirred mixture overnight while allowing temperature to rise to ambient. Cooled to −78° C. and added methanol (50 mL) dropwise. Allowed temperature to again rise to ambient and removed solvent in vacuo. Dissolved residue in methanol (50 mL) and concentrated in vacuo. Dissolved residue in methanol (50 mL) a second time and again concentrated in vacuo to afford a brown foam (1.14 g). Suspended foam in 1.2 N NaOH (10 mL) and methanol (10 mL) and stirred for 16 hours under nitrogen at room temperature. Removed methanol in vacuo and extracted aqueous phase with dichloromethane (2×10 mL). Acidified aqueous phase with 1 N HCl (12 mL) and filtered small amount of brown solid from solution. Concentrated filtrate to afford a white solid (1.58 g). Dissolved product in acetone (40 mL) and filtered NaCl from solution. Concentrated in vacuo to afford a white solid. Obtained 0.89 g (67% yield) of N-[3,4-bis(dihydroxyboryl)]benzoyl-6-aminohexanoic acid. Further purified product by reverse phase HPLC. $^{1}H$ NMR (300 MHz, DMSO-$d_6$-$D_2O$): δ7.97 (doublet, J=1.5 Hz, 1H), 7.69 (doublet of doublets, J=1.9, 7.8 Hz, 1H), 7.61 (doublet, J=7.8 Hz, 1H), 3.20 (doublet, J=6.9 Hz, 2H), 2.18 (triplet, J=7.2 Hz, 2H), 1.48 (multiplet, 4H), 1.26 (multiplet, 2H). $^{13}C$ NMR (300 MHz, DMSO-$d_6$-$D_2O$): δ175.16, 167.47, 133.86, 132.96, 131.54, 126.63, 33.51, 28.64, 25.86, 24.11.

2,5-Dioxopyrrolidinyl N-[3,4-Bis(dihydroxyboryl)]benzoyl-6-aminohexanoic Acid. Dissolved N-[3,4-bis(dihydroxyboryl)]benzoyl-6-aminohexanoic acid (420 mg, 1.30 mmol) and 1,3-propanediol (198 mg, 2.6 mmol) in anhydrous dioxane (20 mL) and heated under reflux to esterify boronic acids for 10 min. Concentrated in vacuo, dissolved in dioxane (20 mL) and again concentrated in vacuo. Repeated concentration twice (to remove residual water generated during the esterification reaction) to finally afford a pale yellow oil. Dissolved oil in dioxane (10 mL) and added N-hydroxysuccinimide (165 mg, 1.43 mmol) followed by 1,3-di-cyclohexylcarbodiimide (295 mg, 1.43 mmol). Stirred for 16 hours at room temperature. Filtered white precipitate (1,3-dicyclohexylurea) from solution and washed with dioxane (2×3 mL). Combined filtrate and washes and concentrated in vacuo to afford a colorless oil. Stirred oil with t-butyl methyl ether at 0° C. to afford a white solid. Obtained 0.35 g (54% yield) of 2,5-dioxopyrrolidinyl N-[3,4-bis(dihydroxyboryl)]benzoyl-6-aminohexanoic acid. $^{1}H$ NMR (300 MHz, DMSO-$d_6$): δ8.42 (triplet, J=5.7 Hz, 1H), 7.87 (doublet, J=1.2 Hz, 1H), 7.72 (doublet of doublets, J=1.8, 7.8 Hz, 1H), 7.45 (doublet, J=7.2 Hz, 1H), 4.07 (triplet, J=5.4 Hz, 4H), 4.05 (triplet, J=5.7 Hz, 4H), 3.21 (doublet of triplets, J=6.0, 6.6 Hz, 2H), 2.79 (s, 4H), 2.65 (triplet, J=6.9 Hz, 2H), 2.00 (multiplet, 4H), 1.63 (multiplet, 2H), 1.52(multiplet, 2H), 1.37(multiplet, 2H). $^{13}C$ NMR (300 MHz, DMSO-$d_6$): δ170.47, 169.19, 166.03, 134.23, 131.42, 130.24, 127.05, 61.71, 30.16, 28.58, 26.84, 25.50, 25.44, 24.00.

EXAMPLE II

Preparation of N'-Amino-N-{[3,4-di(dihydroxyboryl)phenyl]carbonylamino}hexanamide (1,2-PDBA-X-hydrazide)

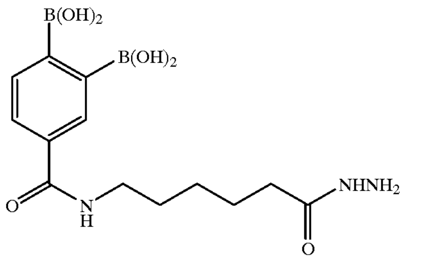

Added t-butyl carbazate (24 mg, 0.18 mmol) to a solution of 2,5-dioxopyrrolidinyl N-[3,4-bis-(dihydroxyboryl)]benzoyl-6-aminohexanoic acid (1,2-PDBA-X-NHS, 90 mg, 0.18 mmol) in dioxane (3 mL) and stirred for 48 hours at room temperature. Added a solution of 4.0 N HCl in dioxane (0.6 mL, 2.4 mmol) and stirred for 12 hours at room temperature. Filtered white precipitate from solution and purified by reverse-phase HPLC (C18, 10% acetonitrile and 90% water containing 0.1% TFA). Combined purified fractions from several runs and concentrated in vacuo to afford a white solid. Obtained 11 mg (14% yield) of N'-amino-N-{[3,4-bis(dihydroxyboryl)phenyl]carbonylamino}hexanamide. $^{1}H$ NMR (300 MHz, DMSO-$d_6$-$D_2O$): δ7.99 (doublet, J=1.8 Hz, 1H), 7.69 (doublet of doublets, J=1.8, 7.8 Hz, 1H), 7.61 (doublet, J=7.8 Hz, 1H), 3.21 (triplet, J=6.8 Hz, 2H), 2.20 (triplet, J=70 Hz, 2H), 1.55 (multiplet, 4H), 1.25 (multiplet, 2H).

EXAMPLE III

Preparation of 1,2-PDBA-AP and 1,3-PDBA-AP Conjugates

Dialyzed Alkaline Phosphatase (AP, 50,000 units) in 2×2 L of bicarbonate buffer (0.1 M $NaHCO_3$, pH 8.3) at 4° C. over 48 hr. Determined concentration of AP dialysate from $A_{280}$ (≈7,700). Conjugated four 1 mL aliquots of AP dialysate (≈4 mg/mL) by adding either a 5-fold or 10-fold molar excess of either 1,2-PDBA-X-NHS (100 mM stock in DMF) or 1,3-PDBA-X-NHS (100 mM stock in DMF). Incubated reactions on ice for 1.5 hr, transferred conjugates to Slide-A-Lyzers (3500 MWCO) and dialyzed in 2×2 L of bicarbonate buffer at 4° C. over 48 hr. Estimated incorporation ratios by comparing the $A_{260}$ (≈4,600 for 1,2-PDBA and ≈2,600 for 1,3-PDBA) to the $A_{280}$ for AP. The results are summarized below in Table 1.

EXAMPLE IV

Enzymatic Activity of 1,2-PDBA-AP and 1,3-PDBA-AP Conjugates

Assayed enzymatic activity with 4-nitrophenylphosphate (pNPP) substrate. Prepared stock solution by dissolving 15 mg of pNPP in 15 mL of 1× DEA buffer (1 M diethanolamine, 1 mM $MgCl_2$, 0.1 mM $ZnSO_4$, pH 10.2). Diluted five 100 μL aliquots of each of the four conjugates to 0.05 μg/mL with 1× TBS buffer (10 mM tris(hydroxymethyl)aminomethane, 140 mM NaCl, pH 8.0) in a multiwell plate, and assayed for AP activity by adding 100 μL of pNPP stock solution to each well and incubating at 37° C. for 10 min. Determined enzymatic activity of conjugates relative to unmodified AP from the average $A_{405}$ value obtained from each of the five aliquots. The results are summarized below in Table 1.

TABLE 1

Preparation and enzymatic activity of Alkaline Phosphatase conjugates.

| PDBA-conjugate | Reagent molar excess | Incorporation ratio (PDBA:AP) | Enzymatic activity (%)[a] |
|---|---|---|---|
| 1,2-PDBA-AP | 5x | 5.0:1 | 71 |
| 1,2-PDBA-AP | 10x | 7.4:1 | 67 |

TABLE 1-continued

Preparation and enzymatic activity of Alkaline Phosphatase conjugates.

| PDBA-conjugate | Reagent molar excess | Incorporation ratio (PDBA:AP) | Enzymatic activity (%)[a] |
|---|---|---|---|
| 1,3-PDBA-AP | 5x | 3.4:1 | 85 |
| 1,3-PDBA-AP | 10x | 6.3:1 | 65 |

[a]Enzymatic activity determined relative to unmodified Alkaline Phosphatase employing 4-nitro-phenylphosphate substrate.

EXAMPLE V

Immobilization of 1,2-PDBA-AP and 1,3-PDBA-AP Conjugates on SHA-X-Sepharose

Equilibrated four low capacity SHA-X-Sepharose columns (0.5 mL, 1.2 μmol SHA/mL gel) and four high capacity SHA-X-Sepharose columns (0.5 mL, 5.2 μmol SHA/mL gel) with 50 mL each of bicarbonate buffer (0.1 M $NaHCO_3$, pH 8.3). Diluted 0.5 mL aliquots of each of the conjugates prepared above to 5 mL total volume with bicarbonate buffer. Loaded conjugates on SHA-X-Sepharose columns by simple gravity-flow, and washed columns with 10 mL of bicarbonate buffer (a sufficient quantity of buffer for the $A_{280}$ to return to baseline). Determined the quantity of conjugate immobilized on each column by subtracting the quantity of conjugate in each of the eluents. The immobilization efficiency of 1,2-PDBA-AP and 1,3-PDBA-AP conjugates on both low capacity and high capacity SHA-X-Sepharose is summarized in Table 2.

TABLE 2

Immobilization of Alkaline Phosphatase by PDBA-AP•SHA-X-Sepharose complex formation involving either 1,2-PDBA-AP or 1,3-PDBA-AP Conjugates.

| PDBA-conjugate | Incorporation ratio (PDBA:AP) | Capacity (μmol SHA/mL) | AP retained (%) |
|---|---|---|---|
| 1,2-PDBA-AP | 5.8:1 | 1.2 | 20 |
| 1,2-PDBA-AP | 8.5:1 | 1.2 | 48 |
| 1,3-PDBA-AP | 3.3:1 | 1.2 | 78 |
| 1,3-PDBA-AP | 6.3:1 | 1.2 | 96 |
| 1,2-PDBA-AP | 5.8:1 | 5.2 | 82 |
| 1,2-PDBA-AP | 8.5:1 | 5.2 | 89 |
| 1,3-PDBA-AP | 3.3:1 | 5.2 | 91 |
| 1,3-PDBA-AP | 6.2:1 | 5.2 | 95 |

EXAMPLE VI

Affinity Chromatography of anti-Alkaline Phosphatase on 1,2-PDBA-AP.SHA-X-Sepharose and 1,3-PDBA-AP.SHA-X-Sepharose Twenty-five milligrams of rabbit anti-Alkaline Phosphatase (αAP) were reconstituted in 5 mL of water and dialyzed in 2×2 L of bicarbonate buffer (0.1 M $NaHCO_3$, pH 8.3) for 48 hr at 4° C. Four milligram aliquots of αAP dialysate were diluted with bicarbonate buffer to a final volume of 5 mL and loaded on each of eight columns, prepared as described above, containing either 0.5 mL of either 1,2-PDBA-AP.SHA-X-Sepharose or 0.5 mL of 1,3-PDBA-AP.SHA-X-Sepharose. Washed columns with 15 mL of bicarbonate buffer, collecting the first 10 mL fraction of each eluent. Determined protein content in each of the fractions from $A_{280}$, and calculated the quantity of αAP retained on each column. Initially, eluted αAP from each column with 15 mL of 50 mM phosphate buffer, pH 11.0 (high pH eluent), collecting a 10 mL fraction into a tube containing 1 mL of 1 M phosphate buffer, pH 5.75. Subsequently, eluted additional αAP from each column with 15 mL of 100 mM glycine HCl buffer, pH 2.5 (low pH eluent), collecting a 10 mL fraction. Adjusted fraction to pH 8–9 by addition of 1 drop of 10 N NaOH. Determined protein content in each of the fractions from $A_{280}$. Analyzed AP, crude αAP, 1,2-PDBA-AP, 1,3-PDBA-AP and affinity purified high pH and low pH αAP fractions by SDS-PAGE on 12.5% gels. Diluted 25 μL aliquots of each fraction with 25 μL of reducing application buffer and heated at 95° C. for 3 min prior to loading 10 μL per lane. Visualized proteins by staining gel with Silver stain (Bio-Rad).

Figure 8:
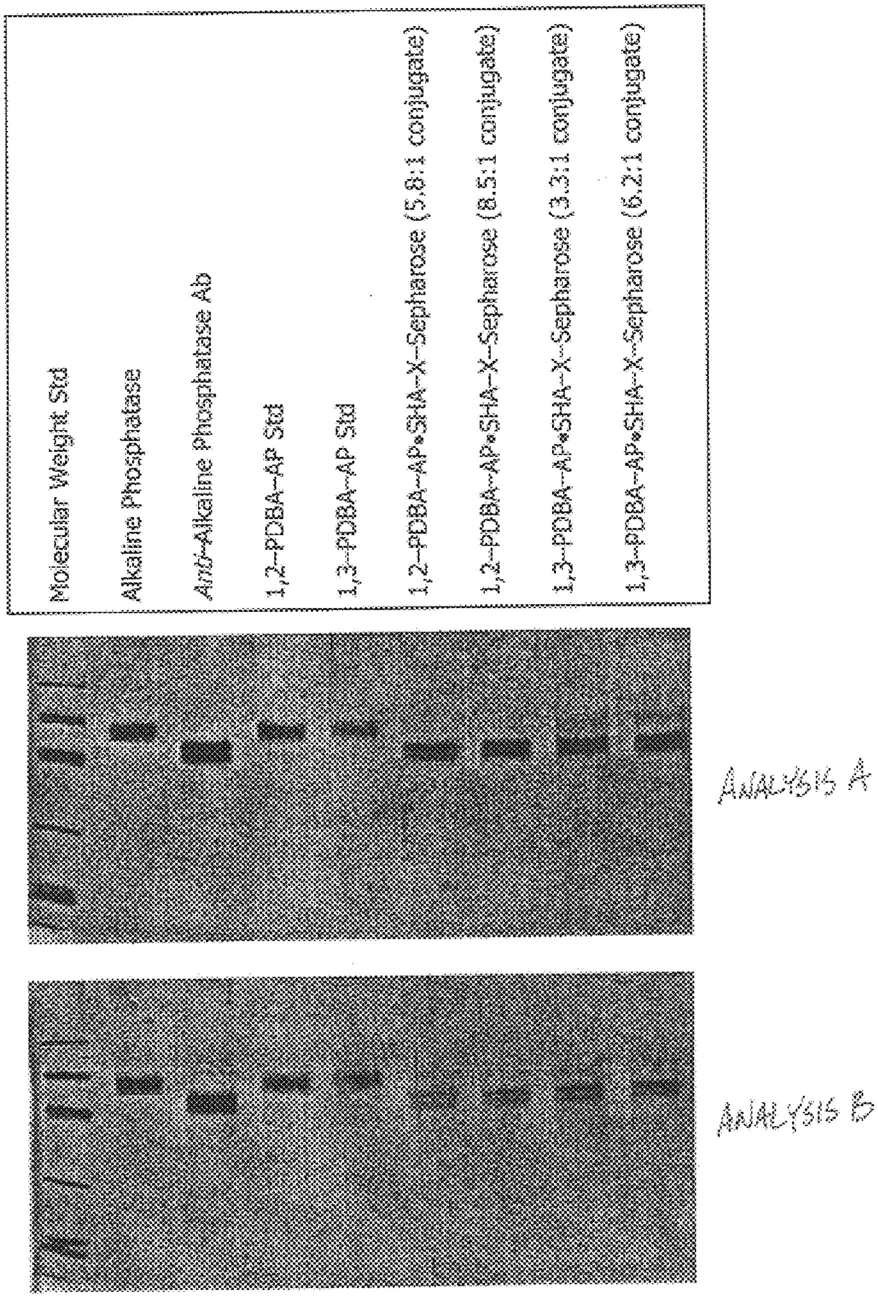
FIG. 8 presents an SDS-PAGE analyses of anti-Alkaline Phosphatase fractions recovered in high pH (11.0) and low pH (2.5) eluents from low capacity (1.2 μmol SHA/mL gel) 1,2-PDBA-AP.SHA-X-Sepharose and 1,3-PDBA-AP.SHA-X-Sepharose columns.

The results obtained for purification of αAP on 1,2-PDBA-AP.SHA-X-Sepharose and 1,3-PDBA-AP.SHA-X-Sepharose are summarized in Table 3. In every instance, AP columns efficiently retained αAP at pH 8.3, which was subsequently recovered in either an alkaline (pH 11.0) or acidic (pH 2.5) eluent. However, in a few instances these results are misleading in that they represent an overestimate with respect to protein recovery. FIG. 8 illustrates the SDS-PAGE analyses of both the high pH and low pH fractions recovered from the low capacity 1,2-PDBA-AP.SHA-X-Sepharose and 1,3-PDBA-AP.SHA-X-Sepharose columns. Analysis A represents fractions recovered at pH 11.0. Analysis B represents fractions recovered at pH 2.5.

Figure 9:
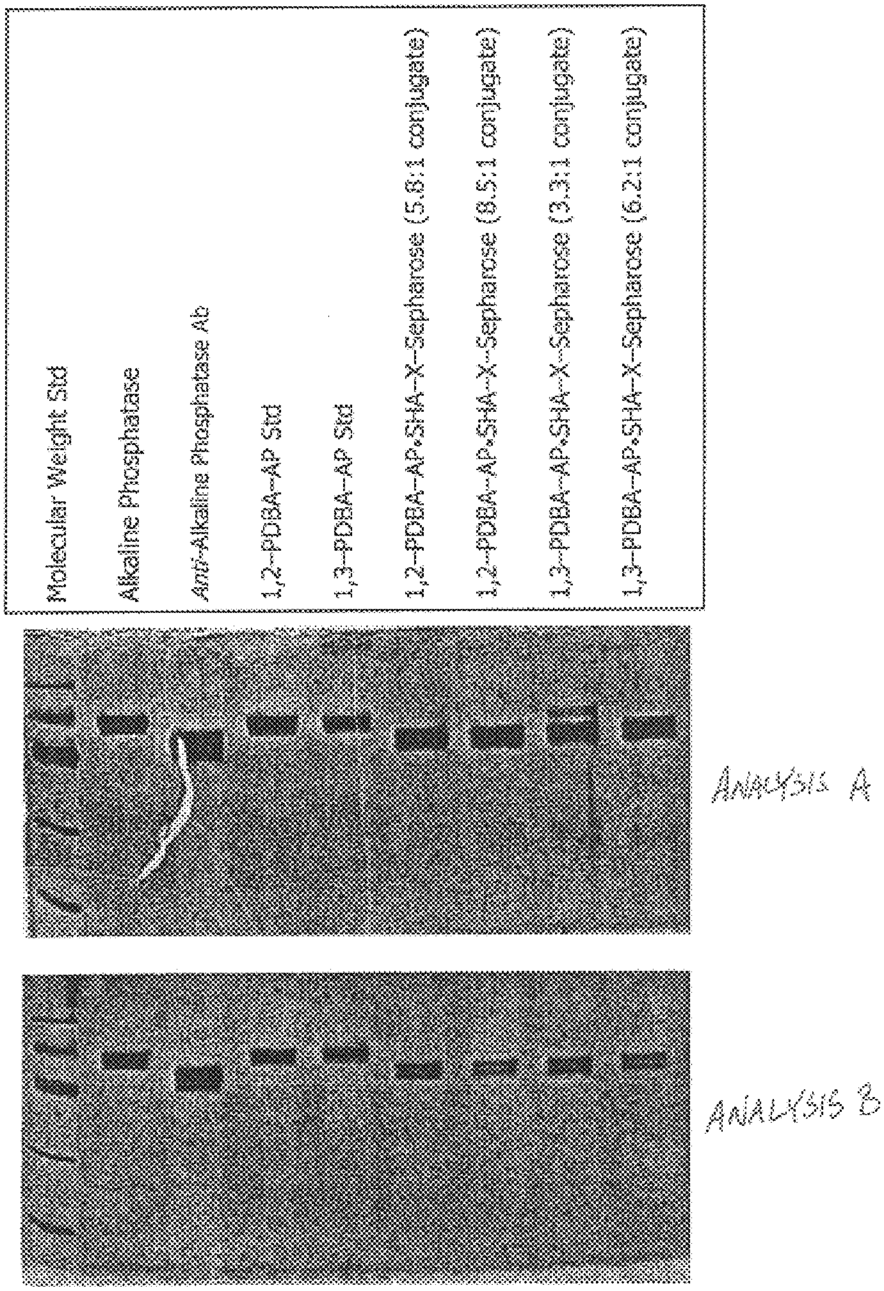
FIG. 9 illustrates the SDS-PAGE analyses of anti-Alkaline Phosphatase fractions recovered in high pH (pH 11.0) and low pH (pH 2.5) eluents from high capacity (5.2 μmol SHA/mL gel) 1,2-PDBA-AP.SHA-X-Sepharose and 1,3-PDBA-AP.SHA-X-Sepharose columns.

FIG. 9 illustrates SDS-PAGE analyses of both the high pH and low pH fractions recovered from the high capacity 1,2-PDBA-AP.SHA-X-Sepharose and 1,3-PDBA-AP.SHA-X-Sepharose columns. Analysis A represents fractions recovered at pH 11.0. Analysis B represents fractions recovered at pH 2.5. 1,3-PDBA-AP conjugates were found to be present as contaminants in both the low pH and high pH fractions recovered from the low capacity SHA-X-Sepharose columns (FIG. 8) as well as the high capacity SHA-X-Sepharose column prepared from the 1,3-PDBA-AP conjugate with the 3.3:1 incorporation ratio (FIG. 9). On the other hand, SDS-PAGE revealed the presence of only trace amounts of contaminating 1,2-PDBA-AP conjugates in both the high pH and low pH fractions recovered from both the low capacity and high capacity 1,2-PDBA-AP.SHA-X-Sepharose columns (FIGS. 8 and 9). From the data presented herein, we conclude that 1,2-PDBA.SHA complexes exhibit superior stability at extremes of pH as compared to 1,3-PDBA.SHA complexes and are consequently preferable when working at under either highly alkaline or highly acidic conditions.

TABLE 3

Affinity Chromatography of anti-Alkaline Phosphatase on 1,2-PDBA-AP•SHA-X-Sepharose and 1,3-PDBA-AP•SHA-X-Sepharose

| PDBA-conjugate | Incorporation ratio (PDBA:AP) | Capacity (μmol SHA/mL) | αAP high pH recovery (%) | αAP low pH recovery (%) | αAP total recovery (%) |
|---|---|---|---|---|---|
| 1,2-PDBA-AP | 5.8:1 | 1.2 | 30 | 32 | 62 |
| 1,2-PDBA-AP | 8.5:1 | 1.2 | 33 | 25 | 58 |
| 1,3-PDBA-AP | 3.3:1 | 1.2 | 50* | 58* | 107* |
| 1,3-PDBA-AP | 6.2:1 | 1.2 | 45* | 57* | 102* |
| 1,2-PDBA-AP | 5.8:1 | 5.2 | 59 | 18 | 76 |
| 1,2-PDBA-AP | 8.5:1 | 5.2 | 35 | 12 | 47 |
| 1,3-PDBA-AP | 3.3:1 | 5.2 | 145* | 51* | 197* |
| 1,3-PDBA-AP | 6.2:1 | 5.2 | 54 | 18 | 72 |

*Represents an overestimate with respect to recovery due to evidence of contaminating conjugate in SDS-PAGE analysis.

What is claimed is:

1. A reagent having the general formula of General Formula I:

General Formula I

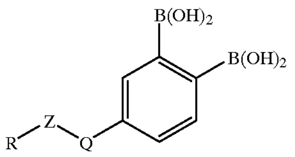

wherein group Z comprises a spacer selected from an aliphatic chain up to about 6 carbon equivalents in length, an unbranched aliphatic chain of from about 6 to 18 carbon equivalents in length with at least one of an intermediate amide and a disulfide moiety, and a polyethylene glycol chain of from about 3 to 12 carbon equivalents in length;

wherein group R is an electrophilic or nucleophilic moiety suitable for reaction of the reagent with a biologically active species; and wherein group Q is one of nothing at all, an amide, a methyl amide, a methylene, an ether, a thioether, a methyl ether, and a methyl thioether moiety.

2. The reagent of claim 1, wherein group R is preferably selected from one of acrylamide, bromo, bromoacetamide, chloro, chloroacetamide, dithiopyridyl, hydrazide, N-hydroxy-succinimidyl ester, N-hydroxysulfosuccinimidyl ester, imidate ester, imidazolide, iodo, iodoacetamide, maleimide, amino and thiol moieties.

3. The reagent of claim 1, wherein group Z is an unbranched alkyl chain of the general formula $(CH_2)_n$, wherein n=1 to 6.

4. The reagent of claim 1, wherein group Q is selected from one of NHCO, CONH, $CH_2$, $CH_2CONH_2$, $CH_2NHCO$, NHCOCH2, $CONHCH_2$, O, $CH_2O$, S, and $CH_2S$ moieties.

5. A conjugate of a biologically active species with a reagent, the conjugate having the general formula of General Formula II:

General Formula II

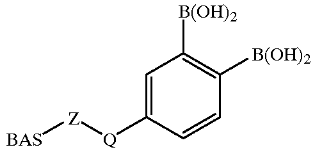

wherein group Z comprises a spacer selected from an aliphatic chain up to about 6 carbon equivalents in length, an unbranched aliphatic chain of from about 6 to 18 carbon equivalents in length with at least one of an intermediate amide and disulfide moiety, and a polyethylene glycol chain of from about 3 to 12 carbon equivalents in length;

wherein group R is an electrophilic or nucleophilic moiety suitable for reaction of the reagent with a biologically active species; and wherein group Q is one of nothing at all, an amide, a methyl amide, a methylene, an ether, a thioether, a methyl ether, and a methyl thioether moiety; and wherein BAS is a biologically active species.

6. The conjugate of claim 5, wherein group Z is an unbranched alkyl chain of the general formula $(CH_2)_n$, wherein n=1 to 6.

7. The conjugate of claim 5, wherein group Q is selected from one of NHCO, CONH, $CH_2$, $CH_2CONH_2$, $CH_2NHCO$, NHCOCH2, $CONHCH_2$, O, $CH_2O$, S, and $CH_2S$ moieties.

8. A bioconjugate comprising a phenylenediboronic acid conjugate bonded through a boronic acid complex to a boronic compound complexing conjugate, the bioconjugate having the general formula of General Formula IV:

General Formula IV

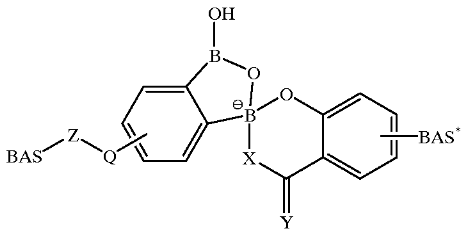

wherein group Z comprises a spacer selected from a saturated or unsaturated chain up to about 0 to 6 carbon equivalents in length, an unbranched saturated or unsaturated aliphatic chain of from about 6 to 18 carbon equivalents in length with at least one of an intermediate amide and a disulfide moiety, and a polyethylene glycol chain of from about 3 to 12 carbon equivalents in length;

wherein group Q is selected from one of nothing at all, an amide, a methyl amide, a methylene, an ether, a thioether, a methyl ether, and a methyl thioether moiety;

wherein group X is selected from one of O, NH, NR', NOH, and NOR", in which R' is selected from one of an alkyl, aryl, alkylaryl, and lower alkylene bearing an electronegative substituent, and in which R" is selected from one of $CH_3$, $CH_2CH_3$, $CH_2CN$, $CH_2CH_2OH$, $CH_2COOH$, $CH_2CONH_2$ and $CH_2OCH_3$;

wherein group Y is selected from one of O, S, and NH; and wherein BAS and BAS* are biologically active species.

9. The bioconjugate of claim 8, wherein group Z is an unbranched alkyl chain of the general formula $(CH_2)_n$, wherein n=1 to 6.

10. The bioconjugate of claim 8, wherein group Q is selected from one of NHCO, CONH, $CH_2$, $CH_2CONH_2$, $CH_2NHCO$, NHCOCH2, $CONHCH_2$, O, $CH_2O$, S, and $CH_2S$ moieties.

11. The bioconjugate of claim 8, wherein group X is NOH.

12. The bioconjugate of claim 11, wherein group Y is O.

13. The bioconjugate of claim 8, wherein BAS and BAS* are different biologically active species.

14. A bioconjugate comprising a phenylenediboronic acid conjugate bonded through a boronic acid complex to a boronic compound complexing conjugate, the bioconjugate having the general formula of General Formula VI:

General Formula VI

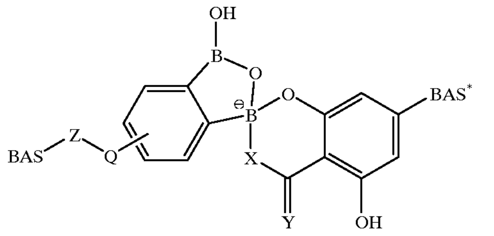

wherein group Z comprises a spacer selected from a saturated or unsaturated chain up to about 6 carbon equivalents in length, an unbranched saturated or unsaturated aliphatic chain of from about 6 to 18 carbon equivalents in length with at least one of an intermediate amide and a disulfide moiety, and a polyethylene glycol chain of from about 3 to 12 carbon equivalents in length;

wherein group Q is selected from one of nothing at all, an amide, a methyl amide, a methylene, an ether, a thioether, a methyl ether, and a methyl thioether moiety;

wherein group X is selected from one of O, NH, NR', NOH, and NOR", in which R' is selected from one of an alkyl, aryl, alkylaryl, and lower alkylene bearing an electronegative substituent, and in which R" is selected from one of $CH_3$, $CH_2CH_3$, $CH_2CN$, $CH_2CH_2OH$, $CH_2COOH$, $CH_2CONH_2$ and $CH_2OCH_3$;

wherein group Y is selected from one of O, S, and NH; and wherein BAS and BAS* are biologically active species.

15. The bioconjugate of claim 14, wherein group Z is an unbranched alkyl chain of the general formula $(CH_2)_n$, wherein n=1 to 6.

16. The bioconjugate of claim 14, wherein group Q is selected from one of NHCO, CONH, $CH_2$, $CH_2CONH_2$, $CH_2NHCO$, NHCOCH2, $CONHCH_2$, O, $CH_2O$, S, and $CH_2S$ moieties.

17. The bioconjugate of claim 14, wherein group X is NOH.

18. The bioconjugate of claim 17, wherein group Y is O.

19. The bioconjugate of claim 14, wherein BAS and BAS* are different biologically active species.

20. A method comprising:

conjugating a 1,2-phenylenediboronic acid molecule and a first bioacive species;

conjugating a boronic compound complexing moiety and a second bioactive species; and conjugating the 1,2-phenylenediboronic acid molecule and the boronic compound complexing moiety.

21. The method of claim 20, wherein the first and second bioactive species are different.

22. The method of claim 20, wherein the first bioactive species is selected from a group consisting of proteins, polysaccarides, hormones, nucleic acids, liposomes, cells, drugs, radionuclides, toxins, haptens, inhibitors, fluorophores, ligands, and solid-phase supports.

23. The method of claim 21, wherein conjugating the phenylenediboronic acid and the first bioacive species comprises conjugating a plurality of phenylenediboronic acid molecules to the first bioactive species.

24. A method of conjugating a bioactive species from a medium comprising;

contacting a 1,2-phenylenediboronic acid molecule with the medium;

conjugating the 1,2-phenylenediboronic acid with at least one bioactive species in the medium at a first site on the phenylenediboronic acid molecule; and conjugating the 1,2-phenylenediboronic acid with a boronic compound complexing moiety at a second site on the 1,2-phenyldiboronic acid molecule.

25. The method of claim 24, wherein the method comprises separating a bioactive species selected from a group consisting of proteins, polysaccarides, hormones, nucleic acids, liposomes, cells, drugs, radionuclides, toxins, haptens, inhibitors, fluorophores, ligands, and solid-phase supports.

26. The method of claim 25, wherein at least one bioactive species is a first bioactive species, and the method further comprising conjugating the boronic compound complexing moiety with at least one second bioactive species.

27. The method of claim 26, wherein the at least one second bioactive species is different from the at least one first bioactive species.

* * * * *